(12) United States Patent
Nix et al.

(10) Patent No.: US 11,174,285 B2
(45) Date of Patent: Nov. 16, 2021

(54) METHODS AND KITS FOR ISOLATING, CAPTURING, AND RECOVERY OF TARGET MACROMOLECULES BY GEL ELECTROPHORESIS

(71) Applicant: Princeton Separations, Inc., Freehold, NJ (US)

(72) Inventors: Paul T. Nix, Jackson, NJ (US); Marcus J. Horn, Cliffwood, NJ (US)

(73) Assignee: Princeton Separations, Inc., Freehold, NJ (US)

( * ) Notice: Subject to any disclaimer, the term of this patent is extended or adjusted under 35 U.S.C. 154(b) by 139 days.

(21) Appl. No.: 16/281,649

(22) Filed: Feb. 21, 2019

(65) Prior Publication Data

US 2019/0389902 A1    Dec. 26, 2019

Related U.S. Application Data

(60) Provisional application No. 62/689,457, filed on Jun. 25, 2018.

(51) Int. Cl.
*G01N 35/10* (2006.01)
*G01N 27/447* (2006.01)
*C07K 1/26* (2006.01)
*C08F 220/56* (2006.01)

(52) U.S. Cl.
CPC .............. *C07K 1/26* (2013.01); *C08F 220/56* (2013.01); *G01N 27/44726* (2013.01); *G01N 27/44739* (2013.01); *G01N 27/44747* (2013.01); *G01N 27/44778* (2013.01); *G01N 35/10* (2013.01); *G01N 2035/1027* (2013.01)

(58) Field of Classification Search
CPC ..... G01N 27/44739; G01N 2035/1027; G01N 35/10
See application file for complete search history.

(56) References Cited

U.S. PATENT DOCUMENTS

| | | | |
|---|---|---|---|
| 4,804,469 A | 2/1989 | Walsh | |
| 4,812,216 A | 3/1989 | Hurd et al. | |
| 4,889,606 A | 12/1989 | Dyson et al. | |
| 4,964,961 A * | 10/1990 | Brautigam | B01D 57/02 204/462 |
| 5,449,446 A | 9/1995 | Verma et al. | |
| 5,585,276 A | 12/1996 | Yom et al. | |
| 7,850,922 B2 * | 12/2010 | Gallagher | G01N 1/10 422/501 |

(Continued)

FOREIGN PATENT DOCUMENTS

BR    201106870 A2 * 11/2013 ................ B43L 7/00

OTHER PUBLICATIONS

Girvitz et al., "A Rapid and Efficient Procedure for the Purification of DNA from Agarose Gels," Analytical Biochemistry 106, 492-496 (1980) (Year: 1980).*

(Continued)

*Primary Examiner* — Alexander S Noguerola
(74) *Attorney, Agent, or Firm* — Hoffmann & Baron, LLP

(57) ABSTRACT

A method of collecting one or more target macromolecules in a capture membrane by gel electrophoresis is disclosed, as well as a kit for macromolecule isolation and recovery including: a preformed gel; a capture device; an insertion guide; and optionally, a migration gauge.

18 Claims, 20 Drawing Sheets

(56) References Cited

U.S. PATENT DOCUMENTS

2006/0060519 A1* 3/2006 Tkacik .................. B01D 69/02
210/321.86

OTHER PUBLICATIONS

Webpage article, author unknown, entitled "Conventional methods for the agarose gel extraction of DNA," BiochemPages, Apr. 11, 2017, downloaded Dec. 2, 2020 from https://www.biochempages.com/2017/04/conventional-methods-agarose-gel-extraction-dna.html#:~:text=Electrophoresis%20on%20DEAE-cellulos (Year: 2017).*
Machine-generated English language translation of Brazilian patent BR 201106870 A2, patented Nov. 2013 (Year: 2013).*
Sambrook et al., "Protocol—Recovery or DNA from Agarose Gels: Electrophoresis onto DEAE-cellulose Membranes," adapted from Molecular Cloning, 3rd edition, by Joseph Sambrook and David Russell, Cold Spring Harbor Laboratory Press, Cold Spring Harbor, NY, USA, 2001, published 2006 (Year: 2006).*
Dretzen et al., A Reliable Method for the Recovery of DNA Fragments from Agarose and Acrylamide Gels, Analytical Biochemistry 112, 295-298 (1981) (Year: 1981).*
Goodwin, Sara, "Preparing extra-long DNA fragments for RS II and Sequel applications," presentation for Pacific Biosciences user group meeting, Jun. 27, 2017 (21 pages).
International Search Report and Written Opinion dated Dec. 2, 2019 issued in International Application No. PCT/US2019/032621 (12 pages).

* cited by examiner

FIGURE 3
FIGURE 4
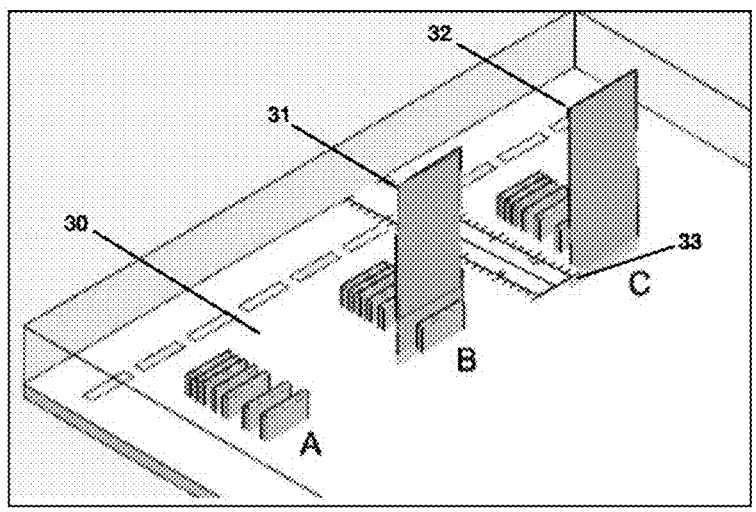
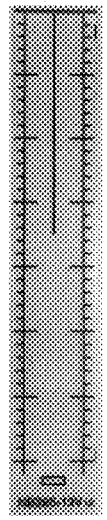
FIGURE 5
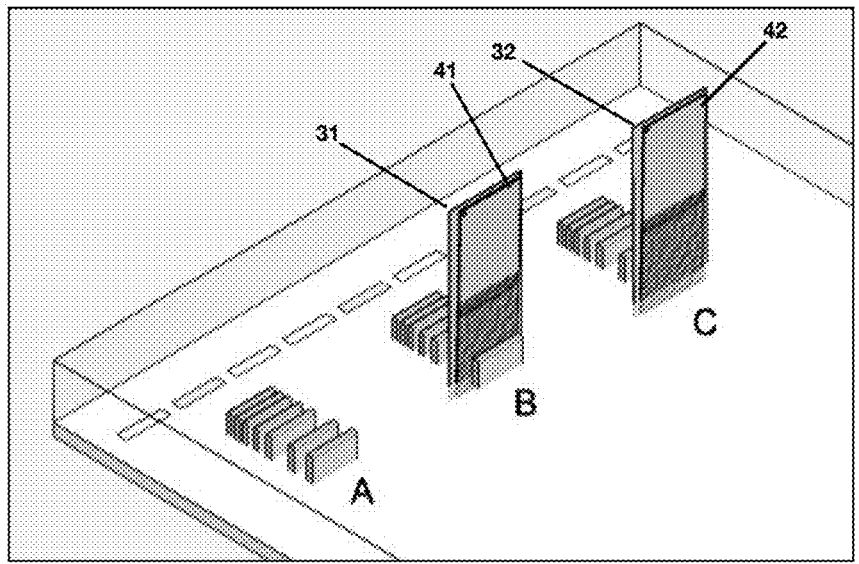

| Size (kb) | N8297-26<br>↓<br>5Jun18<br>(100V 90min) |
|---|---|
| 20.0 | 0.93 |
| 10.0 | 1.10 |
| 8.0 | 1.20 |
| 6.0 | 1.35 |
| 5.0 | 1.44 |
| 4.0 | 1.55 |
| 3.0 | 1.73 |
| 2.0 | 1.97 |
| 1.5 | 2.15 |
| 1.0 | 2.38 |
| 0.5 | 2.71 |

| Size (kb) | N8297-29<br>↓<br>10Jun18<br>(100V 45min) |
|---|---|
| 20.0 | 0.47 |
| 10.0 | 0.56 |
| 8.0 | 0.62 |
| 6.0 | 0.69 |
| 5.0 | 0.74 |
| 4.0 | 0.80 |
| 3.0 | 0.89 |
| 2.0 | 0.99 |
| 1.5 | 1.07 |
| 1.0 | 1.20 |
| 0.5 | 1.35 |

METHODS AND KITS FOR ISOLATING, CAPTURING, AND RECOVERY OF TARGET MACROMOLECULES BY GEL ELECTROPHORESIS

CROSS-REFERENCE TO RELATED APPLICATION

This application claims the benefit of priority from U.S. Provisional Application No. 62/689,457, filed Jun. 25, 2018, the entire contents of which are incorporated by reference herein in entirety.

FIELD OF THE DISCLOSURE

The present disclosure relates to methods and kits for isolation and recovery of one or more macromolecules by electrophoresis methods. Specifically, it relates to methods and kits for the recovery of nucleic acids, proteins and other macromolecules, using a preformed gel and a capture device, including a capture membrane and optionally a holder.

BACKGROUND

Electrophoretic separation of macromolecules, such as deoxyribonucleic acids (DNA) and proteins, has been a routine laboratory technique for more than 40 years. In particular, electrophoretic separation of DNA fragments has found numerous uses in molecular biology, clinical chemistry and medicine, including forensics, diagnostics and sample preparation for DNA sequencing.

While the electrophoretic separation of macromolecules has been an established and routine technique for many years, the isolation of these molecules has remained difficult and non-reproducible. Numerous methods and techniques have been developed over time in an attempt to improve and simplify the isolation of these molecules following separation. However, the success of the isolation remains highly dependent upon the skill of the practitioner.

With the continuing advances in molecular and structural biology, NextGen Sequencing, diagnostics, and medicine, the need for a means to routinely and reproducibly isolate DNA fragments of specific and defined size has grown significantly, as evidenced by the multitude of companies offering devices, kits and reagents targeted towards the isolation of pure or defined fragments of DNA from electrophoresis gels.

Many of the known methods require a first careful excision of the band or bands of interest with a sterile scalpel under ultraviolet or visible light illumination. DNA is then extracted from the preformed gel slice by various means. This first excision process may expose the sample, as well as the user to unnecessary and damaging amounts of ultraviolet radiation. Additionally, the skill of the artisan can influence the amount of excess gel material which may be excised along with the bands of interest, said excess gel contributing variability to the efficiency and reproducibility of the subsequent DNA extraction.

Various mechanical manipulation methods have also been developed for the removal of DNA from gel slices including "freeze and squeeze", "crush and soak" and centrifugal spin techniques. Additionally, gel slices have been dissolved chemically, melted at elevated temperatures, or treated with enzymes which degrade the agarose, followed by entrapment of the DNA onto surfaces, such as silica, ion exchange, etc.

Numerous electroelution devices have been developed for the specific removal of DNA from gel slices. These rely on the capture of the DNA by charged capture membranes, adsorptive surfaces, or impermeable capture membranes. As with mechanical manipulation methods, these devices add substantial additional manipulation to the isolation procedure and with it a risk of significant sample loss, adulteration, and variability.

Each of the prior art methods or devices described above has disadvantages in ease of use, efficiency, cost and usability of the recovered fragments.

Methods have also arisen which are designed to preclude the need for gel slice excision and subsequent elution of DNA from the preformed gel, including "wells in gels" and "direct capture membrane capture" techniques.

There is a need for a method to improve the ease of use and broaden the rate of success of the direct capture membrane capture procedure without the introduction of costly devices or deviation from its basic format. Additionally, there is a need for a method to improve the ease of identifying the location of fragments of interest so as to properly position the capture membrane without undue exposure of the macromolecules of interest to harmful radiation or other potential detrimental interactions.

SUMMARY

A method of capturing one or more target macromolecules in a capture membrane using electrophoresis is disclosed. That method includes: (a) introducing a sample containing a mixture of macromolecules into a sample well at a position on a preformed gel; (b) applying an electric field for a first amount of time across opposing ends of the preformed gel in a first direction causing the mixture of macromolecules in the sample to move through the preformed gel and causing at least one target macromolecule to separate from the remainder of the mixture of macromolecules; (c) stopping the electric field; (d) identifying a position in the preformed gel of the target macromolecule, optionally using a migration gauge; (e) inserting a capture device comprising a capture membrane into the preformed gel in a position in a future pathway of the target macromolecule; and (f) applying the electric field for a second amount of time to the preformed gel in the first direction or a second direction to move the target macromolecule to be collected on the capture membrane. The method may also include the steps of: removing the capture device from the preformed gel, and processing the capture membrane. The step of processing may include recovering one or more target macromolecules or PCR amplification of the target macromolecule, e.g., DNA, directly on the capture membrane. The first direction of the electric field and the second direction of the second electric field may be the same or different, such as perpendicular, i.e., rotated 90 degrees.

Before inserting the capture device into the preformed gel, the method may include the steps of: inserting an insertion guide comprising a locator tab into the preformed gel at a position in the future pathway of the target macromolecule, creating a slit in the preformed gel using the insertion guide with no or minimal damage to the preformed gel, and guiding the capture device along the insertion guide and into the slit, and optionally, removing the insertion guide from the preformed gel. The insertion guide may be made from a plastic, and may be of any color.

The capture membrane may be removably attached or adhered to a support member, with the support member optionally providing increased structural rigidity to the capture membrane, including a handle, and/or including written indicia, such as gauge markings correlating to migration distance. The whole or a part of the capture device may be semi-rigid or rigid.

Also disclosed are kits for isolation and recovery of one or more macromolecules comprising any combination of the following: a preformed gel; a capture device comprising a capture membrane, and optionally, a support member; and an insertion guide, optionally including a locator tab. A migration gauge may also be included in the kit.

BRIEF DESCRIPTION OF THE FIGURES

FIG. 3 is an exemplary depiction showing placement of locator tabs in front of target macromolecules (DNA fragments) using a calibrated DNA migration gauge.

FIG. 4 is a migration gauge.

FIG. 5 is an exemplary depiction showing placement of a capture device directly in front of each locator tab.

FIGS. 13a and b are calibration tables of DNA fragment size versus the measured distance traveled on the preformed gel, as measured using a migration gauge, which can now be used as a guide to locate DNA Locator Tabs in unstained gel.

DETAILED DESCRIPTION

Figure 1:
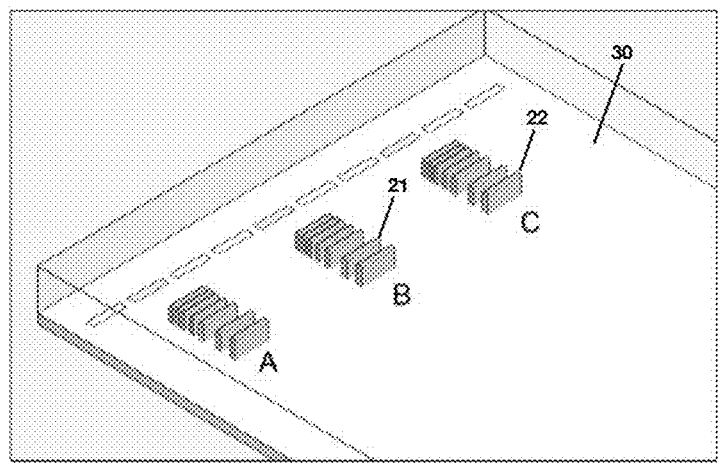
FIG. 1 is an exemplary drawing of separated DNA fragments of three samples in a 1% agarose gel after applying an electric field for 45 minutes.

The present invention provides a new method, an improved insertion guide and capture device, as well as a kit, for the isolation, capture and recovery of macromolecules from gels, in a means that is rapid, easy and convenient to use, and provides high recovery in low volumes.

A method of capturing one or more target macromolecules in a capture membrane is disclosed. That method includes: (a) introducing a sample containing a mixture of macromolecules into a sample well at a position on a preformed gel; (b) applying an electric field for a first amount of time across opposing ends of the preformed gel in a first direction such that the mixture of macromolecules in the sample move through the preformed gel and the target macromolecule separates from the remainder of the mixture of macromolecules; (c) stopping the electric field when the mixture of macromolecules have separated; (d) identifying a position in the preformed gel of the target macromolecule; (e) inserting a capture device comprising a capture membrane into the preformed gel in a position in a future pathway of the target macromolecule; and (f) applying the electric field for a second amount of time to the preformed gel in a second direction to move the target macromolecule on to the capture membrane.

A sample containing a mixture of macromolecules is introduced into a sample well at one end of a preformed gel. Any gel known for use in the art may be used in accordance with the disclosure. For example, the preformed gel may be in the form of a slab or a tube, and may consist of agarose, acrylamide, or a combination thereof, and is in contact with a conductive medium or buffer. A gel of 1% agarose, which may be 1 g agarose plus 100 g of DNA Binding Buffer prepared from concentrate, works well for smaller fragments. The preformed gel may have one or more sample wells therein. The sample wells may be of any size and made by any method known in the art. In the method of the present disclosure, one or more wells of the preformed gel may be filled with one or more samples. For example, one sample may be placed into one well in a preformed gel, one sample may be placed into more than one well, or more than one sample, such as 2, 3, 4, 5 etc., may be tested at the same time such that each well in the preformed gel is filled with one sample.

The sample may contain a mixture of macromolecules. "Macromolecules" as used herein refers to a molecule containing a very large number of atoms, such as a protein, nucleic acid, or synthetic polymer. The macromolecule may be DNA, RNA, proteins, polypeptides, amino acid chains, polysaccharides, oligosaccharides, any fragments thereof, and any combinations thereof. For example, the sample may contain a mixture of DNA and DNA fragments, a mixture of DNA fragments, or a mixture of RNA and RNA fragments.

Each target macromolecule may be selected from the group consisting of: a radioactively labeled macromolecule, chromophorically labeled macromolecule, fluorophorically labeled macromolecule, stained macromolecule, unlabeled macromolecule, and any combination thereof. The labeling may be covalent or non-covalent. Each target macromolecule may be DNA, RNA, proteins, polypeptides, amino acid chains, polysaccharides, oligosaccharides, any fragments thereof, and any combinations thereof After one or more samples is placed in one or more wells in the preformed gel, an electric field is created across opposing ends of the preformed gel, causing the macromolecules within the sample to migrate (in a direction of the electric field) toward the opposite end of the preformed gel. The rate at which each macromolecule (for example, DNA, DNA fragment, RNA, RNA fragment) migrates is a characteristic of that macromolecule, and is dependent upon its length, shape, charge and other characteristics. Macromolecules having similar rates of migration will tend to migrate as a band. Over a period of time of application of the electric field, the sample will separate along a lane into distinct bands, with each band composed of fragments having similar characteristics. Bands may be located and identified by a variety of techniques, including staining, or labeling with radioactive, chromophoric or fluorophoric reagents. According to one method, sometimes referred to as pre-staining, the preformed gel may be premixed with the stain or label during gel preparation, prior to electrophoresis. Such a gel that is premixed with a stain or label may be referred to as a pre-stained gel. Macromolecules separated by a pre-stained gel can be visualized directly with an appropriate viewing device.

According to another method, the macromolecule is mixed with a stain or dye, before placement in, or directly within the sample well prior to the electrophoretic process, in the absence of pre- or post-gel staining. Samples prepared in such manner, sometimes referred to as pre-labeling, may be visualized directly with an appropriate viewing device. According to an alternative method, sometimes referred to as post-gel staining or post-staining, the preformed gel may be stained or labeled with a solution following the electrophoretic process and then viewed with an appropriate viewing device.

To view the preformed gels, bands of separated macromolecules after electrophoresis, and capture devices and capture membranes of the present disclosure, visualization dyes, such as ethidium bromide (EB, EtBr), may be used. EB is visualized using UV excitation light (ultraviolet (UV) radiation) where the DNA complex with EB will fluoresce. Any other visualization dye and light sources known for use in the art may be employed with the methods disclosed herein. SYBR Gold may be used to bind DNA. The resulting DNA-dye complex may be excited with blue LED light and its fluorescence can be detected under an Orange filter.

This first amount of time of applying the electric field is the amount of time required to form distinct bands of separated macromolecules. For example, it may be about 10 minutes to about 10 hours and any time in between. The first amount of time is dependent on the voltage (lower is slower) and the concentration of agarose in the gel (higher concentration presents more obstacles for large macromolecules to get around). The first amount of time may be about 15 minutes to about 500 minutes, about 20 minutes to about 400 minutes, or about 30 minutes to about 120 minutes. The first amount of time may be about 20 minutes, about 25 minutes, about 30 minutes, about 35 minutes, about 40 minutes, about 45 minutes, about 50 minutes, about 55 minutes, about 60 minutes, or about 65 minutes.

The second amount of time of applying the electric field is the amount of time required to electromigrate (i.e., move) the desired macromolecules, which may be one or more target macromolecules, or in some cases, the entire lane of separated macromolecules, completely onto the capture membrane. For example, it may be about 10 minutes to about 360 minutes and any time in between. The second amount of time may be about 15 minutes to about 200 minutes, about 20 minutes to about 120 minutes, about 20 minutes to about 60 minutes, or about 20 minutes to about 45 minutes. The second amount of time may be about 20 minutes, about 25 minutes, about 30 minutes, about 35 minutes, about 40 minutes, about 45 minutes, about 50 minutes, about 55 minutes, about 60 minutes, or about 65 minutes.

The voltage of the first electric field and second electric field may be any known voltage in the art for application in electrophoresis. For example, about 100 volts. The voltage of the first electric field and second electric field may be the same or different. In an embodiment, the first amount of time is about 45 minutes at about 100 volts, and the second amount of time is about 20 to about 45 minutes at about 100 volts.

After the macromolecules have separated into bands along the direction of the first electric field in the preformed gel, the electric field is stopped and the position of the target macromolecule on the preformed gel is identified. Where there are more than one target macromolecule, after the macromolecules have separated into bands along the direction of the first electric field in the preformed gel, the electric field is stopped and the positions of the target macromolecules are identified. As explained above, identification may be performed by using a pre-stained gel, post-gel staining, pre-labeling the sample, or any other method known in the art. Identification may be performed by using a migration gauge, as shown, for example, in FIGS. 3 and 4. The migration gauge provides a means of increasing the precision of the placement of the capture device so as to improve the process of capturing the target macromolecule. FIG. 3 shows a migration gauge 33 placed on top of the preformed gel 30 and next to the target macromolecules to identify placement of insertion guides 31, 32.

The migration gauge may be a standalone component, or it may be incorporated as markings on the capture device or on the preformed gel. The migration gauge is a measuring device for identifying a target molecule based on its migration from a reference point, such as the edge of the sample well. When it is a standalone component, such as shown in FIG. 4, the migration gauge may be made from a plastic. It may be thick enough and made from a selected material to maintain its shape. It may be flexible, semi-rigid, or rigid (i.e., not able to be bent). It may be thin, e.g., about 0.005 to about 0.008 inches, or it may be thicker, e.g., up to about 0.100 inches. The migration gauge may be opaque, translucent, or transparent. The migration gauge may be any length, with ruler-like markings on all or some portion of its length, and the markings may be on one or both sides along the length of the migration gauge. The migration gauge may be about 1 inch to about 8 inches, about 3 inches to about 6 inches, or about 4 inches long. In a certain embodiment, the migration gauge is about 4 inches long, transparent plastic, and has markings on both sides along a portion of its length.

Before use on the sample to identify one or more target macromolecules, the migration gauge may be calibrated. Calibration may be accomplished by running a control (e.g., (SYBR Gold-DNA complex of a sample of DNA Ladder) and creating a calibration table. To calibrate, conduct electrophoresis on a known sample(s) in a preformed gel, run the electric field (e.g., 100V for about 45 min) and observe the patterns of separated bands (e.g., place the preformed gel onto a Blue LED transluminator with required Orange filter to observe a DNA pattern). Then, place the migration gauge on top of the preformed gel above the pattern (aligned with the sample wells). Note the position of the control calibration pattern on the migration gauge and/or photograph the preformed gel for a permanent record. Create a table of known fragment sizes versus the measured distance on the gauge (as shown, for example, in FIGS. 13a and b). The calibrated migration gauge and the calibration table of a list of known fragments at known distances can now be used as a guide to locate target macromolecules in unstained gel lanes as long as the electrophoresis conditions (buffer, voltage and time) are not changed.

In an embodiment, to identify the target macromolecule, the migration gauge is placed on top of the preformed gel, which has undergone electrophoresis, with one end being aligned with the sample well. One way to calibrate the migration gauge is to use one lane of an electrophoresis gel, such as, e.g., lane 1, for a mixture of a DNA Ladder and SYBR® Gold (e.g., 500 ng of 1 kb DNA Ladder plus 0.5 uL of 6X SYBR® Gold). The gel may or may not contain EtBr. A Blue LED transluminator with an Orange filter may be used to visualize DNA-SYBR® Gold complexes in lane 1 and calibrate the migration gauge. Samples containing DNA may be loaded into the other wells, in addition to the DNA Ladder and SYBR gold in lane 1.

When the migration gauge is calibrated for DNA and DNA fragments, it may be referred to as a calibrated DNA migration gauge.

In an embodiment, to identify the target macromolecule, the migration gauge is placed on top of the preformed gel, which has undergone electrophoresis, with one end being aligned with the sample well.

In a next step, a capture device comprising a capture membrane is inserted into the preformed gel in a position in a future pathway of the target macromolecule. That future pathway may be parallel to the first direction of the first electric field or it may be a different direction, such as perpendicular to the first direction, or opposite to the first direction.

The capture device is durable, and inexpensive to obtain and operate. It may be flexible, semi-rigid, or rigid (i.e., not able to be bent). In an embodiment, the capture device is rigid. The capture device may be any shape, including, but not limited to, square, circular, oval, and rectangular. The capture device includes a capture membrane. The capture membrane may be made from any material and according to any method known for use in the art. For example, the membrane may be made from modified paper, modified cellulose acetate, modified polyvinylidene fluoride, other modified membrane materials, or any combination thereof.

The capture membrane may be removably attached or adhered to a support member on one or more sides. The capture membrane and the support member may be removably attached or adhered along one side of the capture membrane in a strip or line. The support member may be larger, smaller or the same size as the capture membrane. A portion of the support member may protrude beyond the capture membrane, e.g., thereby providing a handle or holder portion. The support member may protrude beyond the capture membrane on one side, more than one side, or on all sides, e.g., one side, two sides, three sides, four sides, etc. The support member provides increased structural rigidity to the capture membrane. In part, this increased structural rigidity allows the capture device to be inserted along the insertion guide into the gel with the capture membrane remaining intact and straight.

The support member may be made from a plastic, or inert plastic, and may be rigid. The support member may be any shape, including, but not limited to, square, circular, oval, and rectangular. When the capture membrane is adhered to a rigid support member on 3 or more sides, the capture device is rigid enough to pierce the preformed gel and be inserted therein, without the need for an insertion guide to first create a slit in the preformed gel.

The support member may have some written indicia thereon, which may be gauge markings correlating to a migration distance of certain macromolecules and/or other labelling. For example, the handle may contain written (printed) indicia thereon of sufficient number and relative spacing to allow for the size calculation of unknown DNA fragments when used in the presence of DNA fragments of known size.

The capture device may be of any size though preferably having a length that is equal to or greater than the depth of the preformed gel. The capture device may be about 0.002 to about 0.020 inches, or 0.010 to about 0.015 inches, in thickness. The capture device may comprise a capture membrane being about 0.001 to about 0.010 inches, about 0.005 to about 0.010 inches, or about 0.008 inches in thickness. The capture device may comprise a support member being about 0.001 to about 0.010 inches, about 0.004 to about 0.009 inches, about 0.005 to about 0.007 inches, about 0.005 inches, or about 0.007 inches in thickness.

The capture device may be about 0.375 to about 2.0 inches, about 0.3 to about 0.5 inches, about 0.5 inches to about 1.5 inches, or about 1.0 inches in length. The capture device may be about 0.1 to about 4.0 inches, about 0.3 to about 3.0 inches, about 0.3 to about 2.0 inches, about 0.5 to about 2.0 inches, about 0.4 to about 1.2 inches, about 0.3 to about 1.0 inches, about 0.4 inches, or about 1.2 inches, in width. The capture device may be of any size though preferably having a width equal to or greater than the width of the band or bands to be captured. The capture device may be about 0.3 to about 0.4 inches wide, and about 0.5 to about 1.5 inches, or about 1 inch in length. The capture membrane may be about 0.4 to about 2.0 inches in width, and/or about 0.2 to about 0.8, or about 0.3 to about 0.5 inches in length. For direct processing, the capture device may be about 1 inch in length, 0.008 inches thick, and 0.40 inches wide. For orthogonal processing, the capture device may be about 1 inch in length, 0.008 inches thick, and 1.20 inches wide. When the capture device is about 1 in length, the capture membrane may be less than about 0.5 inches in length and the handle may be more than about 0.5 inches in length.

Figure 38A:
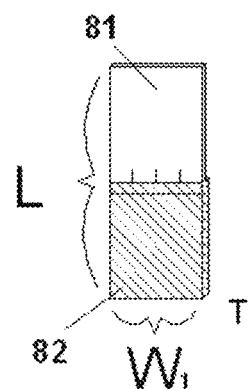
FIG. 38a-c are drawings of a capture device including a capture membrane and a support member.
Figure 38B:
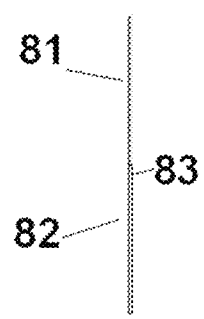
Figure 38C:
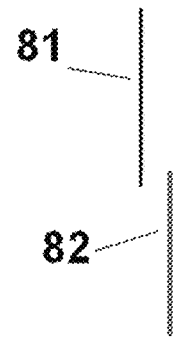

FIGS. 38a, b, and c are drawings of a capture device including a capture membrane 82 and a support member 81. FIG. 38b is the side view of the fully assembled capture device including a capture membrane 82 and a support member 81. The capture membrane 82 and the support member 81 in FIG. 38b are adhered along a strip 83 of overlap. FIG. 38c is the side view of a partially disassembled capture device where the capture membrane 82 has been separated from the support member 81.

In FIG. 38a, the capture device has length L, width $W_1$, and thickness T. The capture membrane 82 is a porous membrane that binds the target macromolecule using physical attributes (e.g., ion exchange, hydrophobic surface properties, etc.). The support member 81 may be a clear plastic material that functions as a handle, and is physically attached to the capture membrane, thereby providing the capture membrane with some increased structural rigidity.

The capture device may be used to collect one target macromolecule; it may be used to collect more than one target macromolecule; it may be used to collect one or more target macromolecules and one or more other (undesired) macromolecules from the sample.

Optionally, before inserting the capture device, an insertion guide comprising a locator tab may be inserted into the preformed gel in the future pathway of the target macromolecule to create a slit in the preformed gel with no or minimal damage to the preformed gel. As such, it may act as a placeholder for the capture device, which may be guided along the insertion guide and inserted into the slit that has been created in the preformed gel. The insertion guide may be flexible, and semi-rigid (i.e., have some rigidity; more rigid than a conventional piece of white computer paper). The insertion guide may have one or more sharp corners or edges which can be used to pierce the preformed or electrophoresis gel. The insertion guide may have one or more sharp corners and be of sufficient rigidity to pierce the preformed gel with one of the one or more sharp corners.

The insertion guide may comprise an inert plastic. It may be a colored plastic of any color, such as, but not limited to, blue, green, red, purple, orange, black. The insertion guide may be of any size though preferably the same size or smaller in length than the preformed gel. The insertion guide may be wider (preferably by less than about 0.5 inches) than the capture device so that it creates a pocket that the capture device fits into comfortably. The insertion guide may be about 0.3 to about 3.0 inches in width, about 0.5 to about 2.0 inches in length, and/or about 0.001 to about 0.01 inches in thickness. The insertion guide may be about 0.5 inches in width, about 1.0 inches in length, and about 0.005 inches in thickness.

The insertion guide may be inserted into the preformed gel adjacent to the identified band of the target macromolecule, such as directly in front of the band, behind the band, or to one side of the band. When inserted, the insertion guide and the well may form an angle of about 0° to about 180°, or about 0° to about 90°. The positioning of the insertion guide is important for good results since it is a placeholder for the capture device. When inserting the insertion guide into the preformed gel, the surface of the preformed gel may be cut/pierced with the corner of the insertion guide and then the rectangular end of the insertion guide may be moved through the gel to the bottom of the preformed gel until it rests on the bottom of the preformed gel tray. The insertion guide may be placed in parallel to the sample well and the band, and inserted directly in front of the band of the target macromolecule.

A capture device may be inserted into the lane of the preformed gel by positioning it behind or in front of the insertion guide and sliding it down the back or the front of the insertion guide until it stops at the bottom of the preformed gel.

The capture device may be moistened with a buffer (such as any known electrophoresis binding buffer) before inserting it into the preformed gel. After inserting the capture device into the preformed gel, the insertion guide may be removed and disposed of leaving the capture device in its place (as shown, for example, in FIG. 6). Disposal after a single use prevents any cross contamination. This may be repeated for each target macromolecule band of interest, keeping track of the lane number.

More than one capture device, with or without the aid of an insertion guide, may be inserted into the preformed gel. Any number of capture devices and insertion guides may be used to collect the desired number of target macromolecules from any one sample. For example, one sample may contain two or more target macromolecules. Then after application of the first electric field, an insertion guide may be placed in front of the band of each target macromolecules so that each may be collected on a different capture device.

In another embodiment, multiple wells on a preformed gel may be filled with samples being the same or different from each other, and then, after application of the first electric field, an insertion guide may be placed in front of each of the target macromolecules on each of the samples before inserting the capture devices. For example, when three wells were filled with three samples, being the same or different from each other, three lanes of separated macromolecules are created upon application of the electric field. Then, an insertion guide may be placed in the future pathway of one or more target macromolecules in each of the lanes. After the insertion guides are inserted into the preformed gel and locations documented, a capture device is guided into position behind or in front of each of the insertion guides and, if used, the migration gauge is removed.

Accordingly, in an embodiment, the method of the disclosure further comprises the steps of: identifying a position on the preformed gel of a second target macromolecule; and inserting a second capture device comprising a second capture membrane in the preformed gel in a position in a future pathway of the second target macromolecule. This may optionally also include the steps of: identifying a position on the preformed gel of a third target macromolecule; and inserting a third capture device comprising a third capture membrane in the preformed gel in a position in a future pathway of the third target macromolecule. These steps may be repeated for any desired number of target macromolecules. Further, before inserting the second/third/fourth, etc. capture device, another insertion guide comprising a locator tab may be inserted into the preformed gel at a position in the future pathway of the target macromolecule creating a slit in the preformed gel, and the another capture device may be guided along the insertion guide thereby inserting the capture device into the slit. After inserting the additional capture devices into the preformed gel, the insertion guides are removed from said gel in any order before applying the second electric field for the second amount of time to move the target macromolecules in the direction of the inserted capture devices to collect the target macromolecules in the capture membranes. One or more capture devices may be used to intentionally capture undesired macromolecules.

The target macromolecule being collected in the capture membrane, means that the target macromolecule, or target macromolecules, is captured in or adhered to the capture membrane, in whole or in part, as desired.

Figure 2:
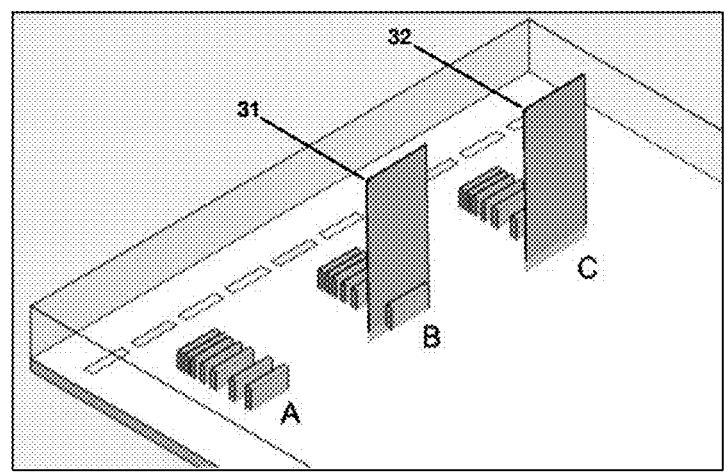
FIG. 2 is an exemplary depiction showing placement of locator tabs in front of target macromolecules (DNA fragments).
Figure 6:
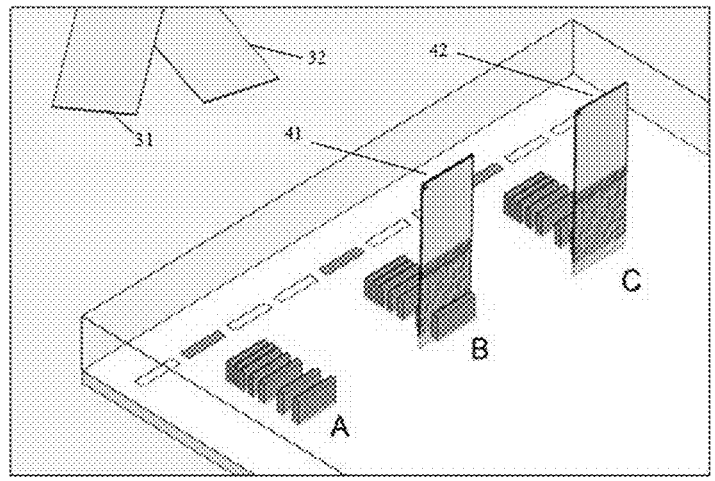
FIG. 6 is an exemplary depiction showing removal of the locator tabs.
Figure 7:
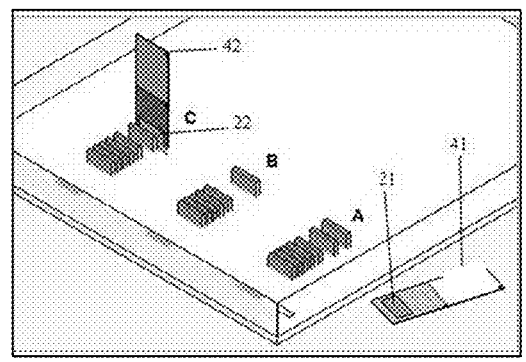
FIG. 7 is an exemplary depiction showing migration of the target macromolecules into the capture devices after application of the electric field for an additional 10 minutes (55 minutes total) and removal of the capture device from lane B.
Figure 8:
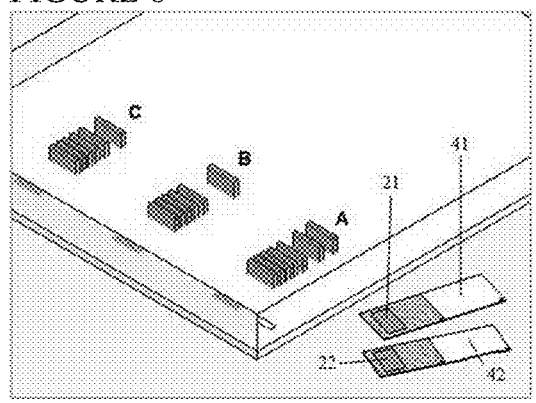
FIG. 8 is an exemplary depiction showing migration of the target macromolecules onto the capture devices after application of the electric field for an additional 10 minutes (55 minutes total as in FIG. 7) and removal of the capture devices from lanes B and C.
Figure 9:
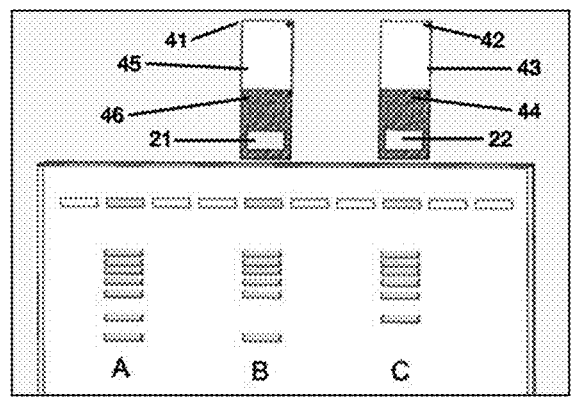
FIG. 9 is a top down view of the preformed gel pattern after removal of the target macromolecules in lanes B and C onto the two capture devices.

FIG. 1 shows target macromolecules 21, 22 in bands along the preformed gel 30 amongst the separated macromolecules of three samples following a first electrophoresis. FIG. 2 shows placement of insertion guides 31, 32 parallel to the bands and directly in front of the target macromolecules 21, 22 from FIG. 1. FIG. 5 shows capture devices 41, 42 placed directly in front of insertion guides 31, 32. FIG. 6 shows removal of the insertion guides 31, 32, leaving capture devices 41, 42 in place in front of the target macromolecules 21, 22 identified in FIG. 1. Following a second electrophoresis, the target macromolecules 21, 22 move on to the capture devices 41, 42 and are collected in the capture membrane 44, 46 as shown in FIGS. 7-9. Each capture device 41, 42 includes a capture membrane 44, 46 and support member 43, 45, which is attached to the capture membrane 44, 46 along one side in a narrow strip of overlap.

In an embodiment, the method of capturing one or more target macromolecules in a capture membrane, comprising the steps of: a) performing electrophoresis for a first amount of time in a first direction across opposing ends of a preformed gel to separate a sample containing a mixture of macromolecules; b) identifying a position of one or more target macromolecules through a visualization process, optionally using a migration gauge; c) piercing the preformed gel with an insertion guide being a locator tab, creating a slit at a position immediately forward of, and in the future pathway of, the target macromolecule, in a manner such that the locator tab is parallel to the band containing the target macromolecule; d) without removing the locator tab, inserting a capture device into the same slit as the locator tab, immediately adjacent and parallel to the locator tab; e) removing the locator tab without any effect on the positioning of the capture device; f) optionally repeating steps c, d and e, with a separate insertion guide and capture device for each target macromolecule that is to be captured and processed; g) restarting the electrophoresis in the same direction as the first direction of electrophoresis, until the target macromolecule(s) is collected in the capture membrane; and h) optionally, removing the capture device for processing.

In another embodiment, the method of capturing one or more target macromolecules in a capture membrane, comprising the steps of: a) performing electrophoresis for a first amount of time in a first direction across opposing ends of a preformed gel to separate a sample containing a mixture of macromolecules; b) identifying a position of one or more target macromolecules through a visualization process, optionally using a migration gauge; c) piercing the preformed gel with an insertion guide being a locator tab, creating a slit at a position immediately forward of, and in the future pathway of, the target macromolecule, in a manner such that the locator tab is perpendicular to the band containing the target macromolecule; d) without removing the locator tab, inserting a capture device into the same slit as the locator tab, immediately adjacent and parallel to the locator tab; e) removing the locator tab without any effect on the positioning of the capture device; f) optionally repeating steps c, d and e, with a separate insertion guide and capture device for each target macromolecule that is to be captured and processed; g) starting electrophoresis in the a second direction that is perpendicular to the first direction of electrophoresis, until the target macromolecule(s) is collected in the capture membrane; and h) optionally, removing the capture device for processing. Processing may include recovering one or more target macromolecules from the capture membrane, or PCR amplification of the target macromolecule, e.g., DNA, directly on the capture membrane. The second electrophoresis process (step g)) may be achieved by using any device capable of multidimensional electrophoresis, or by the reorientation of the preformed gel within a same or different apparatus, which may require removal (cutting of) a portion of the preformed gel so that it fits into the device upon reorientation.

A special Single Well comb may be used when casting the preformed gel. This has a main sample well, which is deeper and larger and can hold 20-30 uL of a sample, and it has flanking mini combs, which form smaller, shallow wells that hold about 10 uL of dyed tracker molecules, such as DNA size markers. The macromolecules in the sample and the DNA size markers migrate through the gel at different heights due to the depth of the mini wells compared to the main sample well. After preparing the gel, the electrophoresis setup, having loaded the gel with sample, and loaded DNA size markers and controls as needed, the sample is electrophoresed setting up a DNA pattern in the gel based on molecular size. In this embodiment, the DNA markers and running dye are used to estimate the approximate location of the DNA sample pattern.

Figure 10:
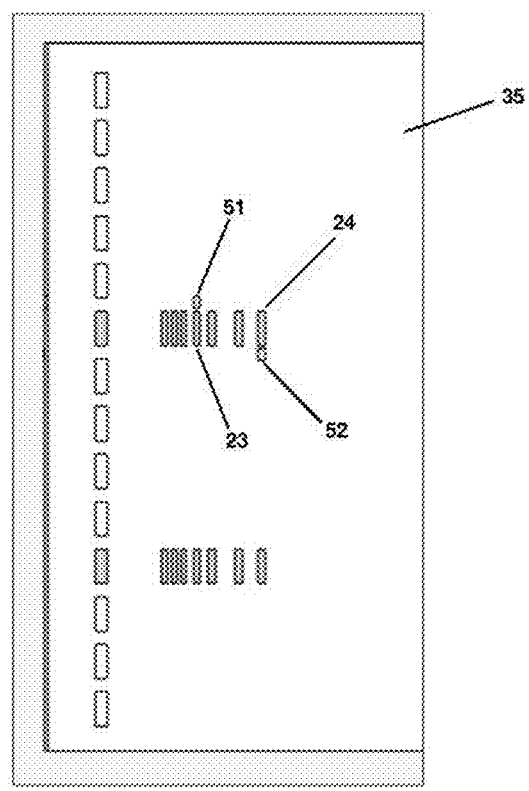
FIG. 10 is a top down view of the preformed gel having 14 wells and 2 samples that have separated into DNA fragment patterns after applying an electric field for 45 minutes at 100 volts; two individual fragments having been additionally marked using tracker dyes.
Figure 11:
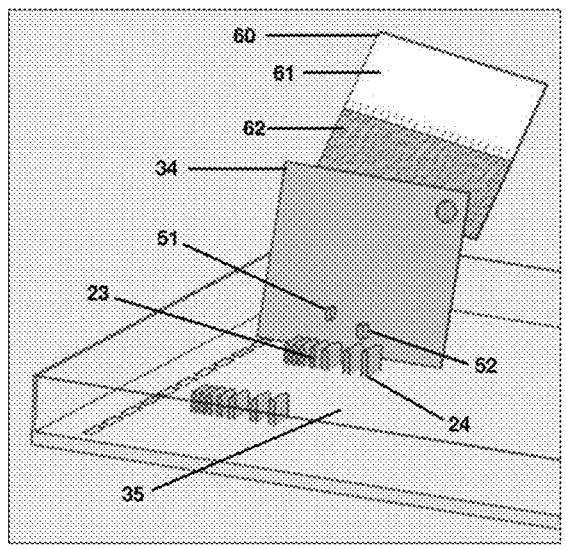
FIG. 11 is the preformed gel of FIG. 10 with the insertion guide placed in the preformed gel perpendicular to the movement of the first electric field, and adjacent to and in the future pathway of the separated macromolecules of the first sample, and the capture device being inserted into the preformed gel in front of the insertion guide.
Figure 12:
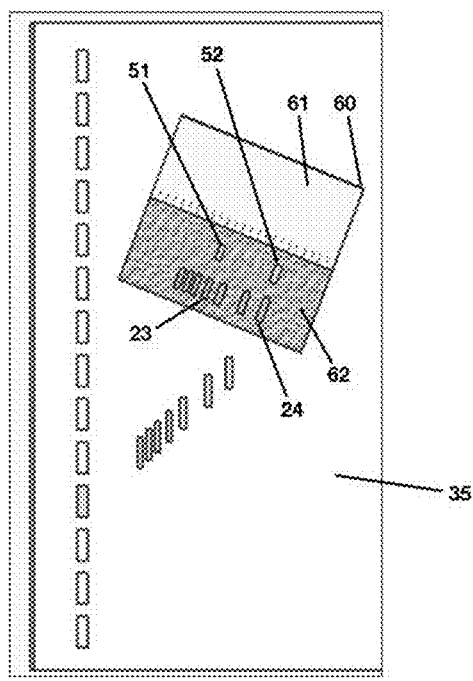
FIG. 12 shows the capture device of FIG. 11 and the separated macromolecules from the first sample being bound to the capture membrane, after applying a second electric field (perpendicular to the first electric field).

FIG. 10 shows target macromolecules 23, 24 in bands along the preformed gel 35 amongst the separated macromolecules of two samples following a first electrophoresis. Also shown are tracker dyes 51, 52, which are used to show the location of the target macromolecules. FIG. 11 shows placement of the insertion guide 34 into the preformed gel 35 perpendicular to the bands and to the side of the lane of separated bands of the sample including target macromolecules 23, 24. Capture device 60 including a capture membrane 62 and support member 61, which extends the full length of the capture device along the backside of the capture membrane 62, is being placed directly in front of the insertion guide 34. Following a second electrophoresis, FIG. 12 shows the lane of separated macromolecules, including the target macromolecules 23, 24, and the tracker dyes 51, 52, having moved onto the capture device 60 and collected in the capture membrane 62.

As such, the latent sample pattern is on the bottom portion of the capture membrane and latent tracker dye or marker DNA pattern is on the upper portion of the capture membrane. In an embodiment, the bottom portion may be set aside for later elution of sample DNA and the upper part may be stained with dye in a bath of EtBr (for fluorescent detection) and/or Crystal Violet, e.g., 0.64 mg/mL (for visible detection). The upper portion of the membrane may be stained for 2 minutes in the stain bath, then washed with running water and finally washed with 95% ethanol. The stained upper portion may be observed under UV light and the bound DNA markers marked with pencil. The position of the marker may be measured from the built in gauge on the capture device and recorded (3 kb marker (above) at 3.2 gauge units, 0.5 kb DNA Ladder (below) at 7.2 gauge units.

In another embodiment, the method of capturing one or more target macromolecules in a capture membrane, comprising the steps of: a) performing electrophoresis for a first amount of time in a first direction across opposing ends of a preformed gel to separate a sample containing a mixture of macromolecules in a lane; b) identifying a position of one or more target macromolecules through a visualization process, optionally using a migration gauge; c) piercing the preformed gel with a capture device, creating a slit at a position immediately forward of, and in the future pathway of, the target macromolecule, in a manner such that the capture device is perpendicular to the band containing the target macromolecule; d) starting electrophoresis in the a second direction that is perpendicular to the first direction of electrophoresis, until at least a portion of, or the whole of, the lane of separated macromolecules, including at least one target macromolecule, is collected in the capture membrane; and e) removing the capture device, optionally, for future processing. Instead of step c, an insertion guide may be used to pierce the preformed gel to create a slit into which the capture device may be subsequently inserted. The insertion guide may be removed after insertion of the capture device and before step d. The methods disclosed herein wherein the second occurrence of electrophoresis is run a second direction that is perpendicular to the first direction of electrophoresis may also be referred to as orthogonal processing.

In an embodiment, the method of capturing one or more target macromolecules in a capture membrane, comprising the steps of: a) performing electrophoresis for a first amount of time in a first direction across opposing ends of a preformed gel to separate a sample containing a mixture of macromolecules; b) identifying a position of one or more target macromolecules through a visualization process, optionally using a migration gauge; c) piercing the preformed gel with an insertion guide being a first locator tab, creating a slit at a position immediately forward of, and in the future pathway of, the target macromolecule, in a manner such that the first locator tab is parallel to the band containing the target macromolecule; d) without removing the first locator tab, inserting a first capture device into the same slit as the first locator tab, immediately adjacent and parallel to the first locator tab; e) piercing the preformed gel with a second insertion guide being a second locator tab, creating a slit at a position immediately forward of, and in the future pathway of, an undesired macromolecule, in a manner such that the locator tab is parallel to the band containing the target macromolecule, and will block the capture of the undesired macromolecule on the first capture device; f) without removing the second locator tab, inserting a second capture device into the same slit as the second locator tab, immediately adjacent and parallel to the second locator tab; g) starting electrophoresis in a second direction, until the target macromolecule(s) is collected in the first capture membrane; and h) optionally, removing the first and/or second capture devices for future processing. The second direction may be the same as the first direction of electrophoresis. In this embodiment, the second capture membrane collects undesired macromolecules from also being collected on the first capture membrane.

Following capture of the target macromolecule, the capture device may be removed from the preformed gel, optionally, when present, the capture membrane may be separated from the support member, and the capture membrane may be processed according to any method known in the art to elute the target macromolecule. Elution from the membrane is generally accomplished with minimal amounts of solution, leading to a high concentration of the desired fragment. When desired, the capture membrane may be cut to separate the adhered macromolecules or for any other propose before elution.

Another embodiment is a capture device for collecting one or more target macromolecules. The capture device includes a capture membrane and a support member comprising a plastic that provides increased structural rigidity to the capture membrane.

The terms used in connection with this embodiment have the same meanings and definitions as defined above.

Another embodiment is a kit for macromolecule isolation and recovery comprising: a capture device comprising a capture membrane; an insertion guide; and a migration gauge. The capture membrane may be removably attached or adhered to a support member, and/or the insertion guide may include a locator tab. The kit may include a preformed gel and/or written instructions. The kit may also include one or more additional components selected from the group consisting of: electrophoresis binding buffer concentrate, electrophoresis binding buffer, elution buffer, spinfunnel, collection tube, molecular-weight size marker and reagent. Electrophoresis binding buffer concentrate, electrophoresis binding buffer, elution buffer, collection tube, molecular-weight size marker and reagent are readily understood by those of ordinary skill in the art. A spinfunnel is a plastic tube which is retained in a collection tube and holds a capture membrane during an elution process.

The terms used in connection with this embodiment (i.e., a kit) have the same meanings and definitions as discussed above.

The features and advantages of the present invention are more fully shown by the following examples which are provided for purposes of illustration, and are not to be construed as limiting the invention in any way.

EXAMPLES

Example 1

Four samples were prepared for agarose gel electrophoresis:
A. 100 ng of 20 kb DNA fragment and 500 ng of 1 kb DNA Ladder
B. 1 ug 5 kb DNA fragment
C. 100 ng 20 kb DNA fragment and 100 ng 5 kb DNA fragment
D. 900 ng sheared genomic DNA (20 kb Shear)

Figure 14:
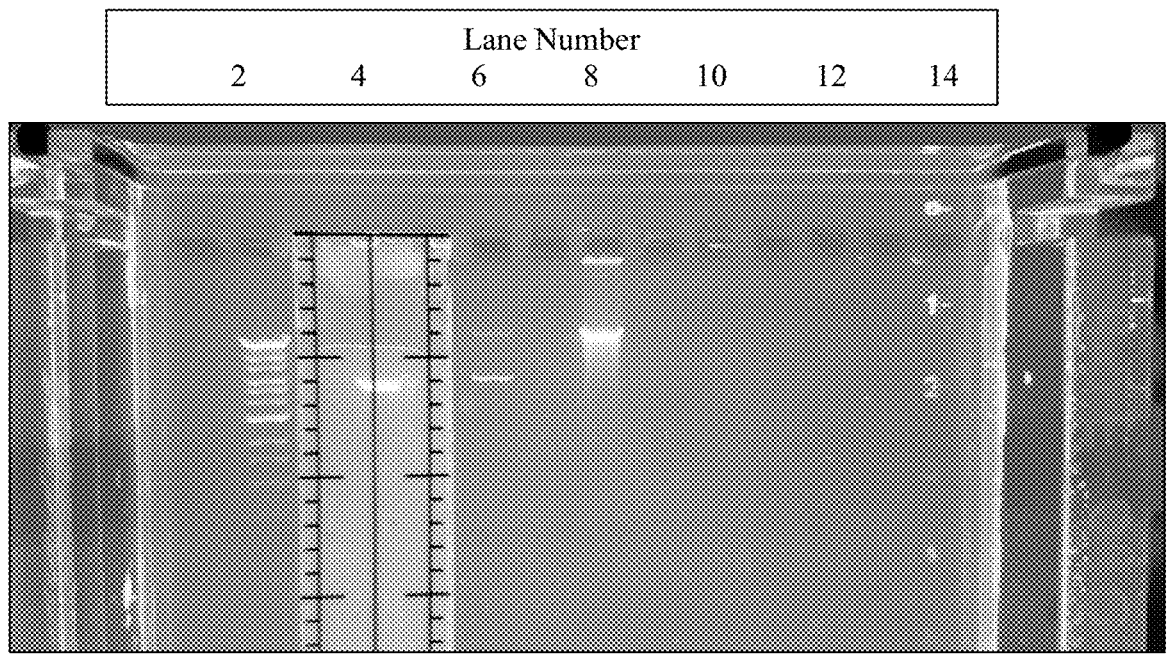
FIG. 14 is a photograph of a pre-stained gel containing EtBr viewed under UV light following a first electrophoresis of a set of four samples and with a migration gauge being used for identification of target DNA fragments and placement of locator tabs.

Samples A-D were loaded into lanes 2, 4, 6 and 8, respectively, of a 14-well 0.8% agarose pre-stained gel containing EtBr. Gel electrophoresis was run at 100V for 45 minutes. The preformed gel tray with gel was removed from the electrophoresis chamber and was placed over a UV light source and visualized using the appropriate filter. A migration gauge was placed onto the preformed gel, and notations were made, using the indicia on the gauge, of the migration positions of the 5 kb and 8 kb standards in lane 2, as in FIG. 14, and lane 6 (5 kb and 20 kb). From these migration positions, insertion locations for the locator tabs were determined, so as to capture a 5 kb band (from lane 4) and a 8-20 kb band range (from lane 8). Locator tabs were placed into lanes 4 and 8 of the preformed gel, in locations so as to capture a 5 kb and a 8-20 kb band range, respectively.

Figure 15:
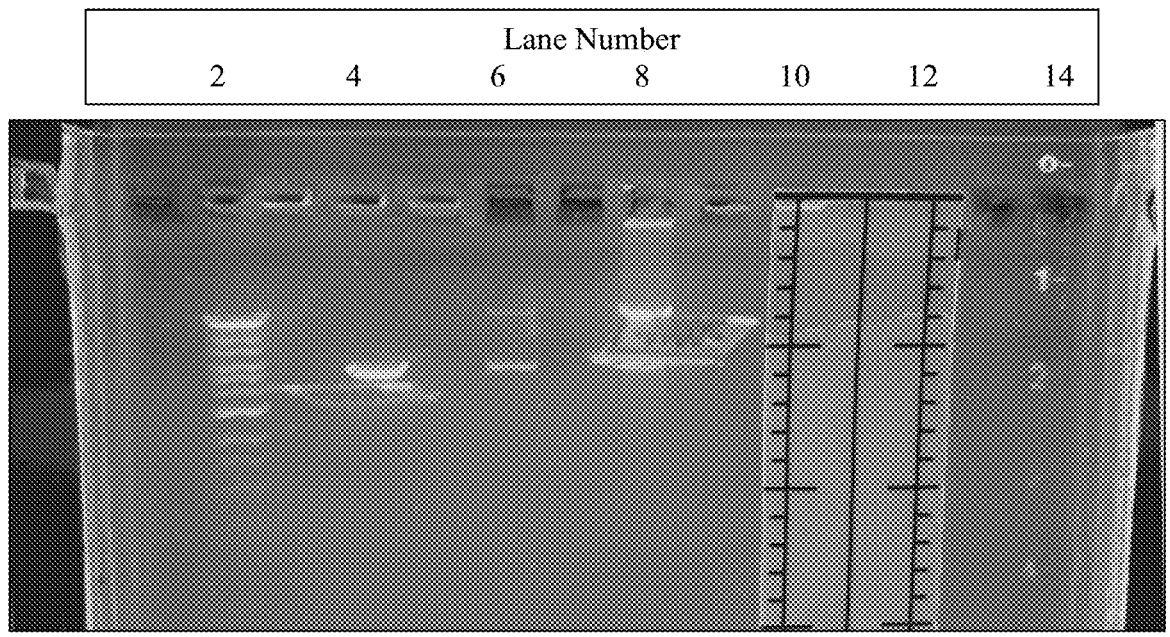
FIG. 15 is a photograph of the same pre-stained gel as shown in FIG. 14 containing EtBr viewed under UV light following a first electrophoresis of the set of four samples with two capture devices in place at positions identified using the migration gauge to capture a 5 kb fragment and an 8-20 kb DNA fragment range.
Figure 16:
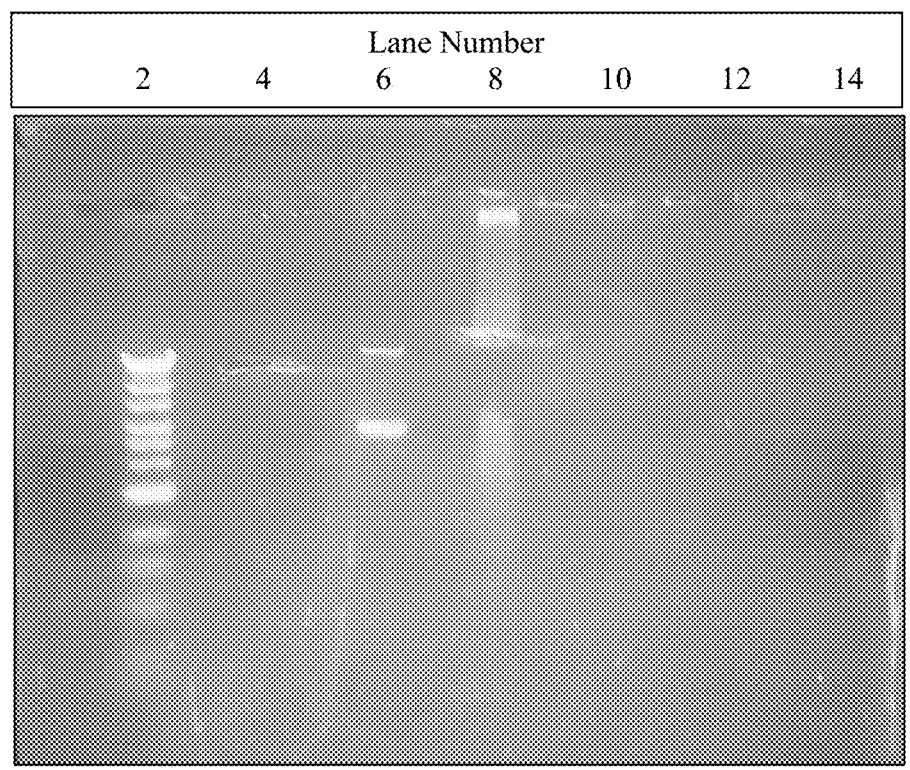
FIG. 16 is a photograph viewed under UV light of a pre-cast stained gel containing EtBr following a second electrophoresis of a set of four samples and after removal of capture membranes in place at locations to capture a 5 kb fragment (Ln4) and an 8-20 kb DNA fragment range (Ln8).

Capture devices, including capture membranes and rigid support members (each attached along one side of the capture membrane in an adhered strip) were inserted behind the locator tabs and the locator tabs were then removed, leaving the capture devices in place in the preformed gel (FIG. 15). The preformed gel containing the capture devices was returned to the electrophoresis chamber, and a second electrophoresis was run at 100V for 30 minutes to capture the 5 kb band and the 8-20 kb range DNA on the capture devices. After removal of the capture devices, the preformed gel tray with gel was removed from the electrophoresis chamber and was placed over a UV light source and visualized using the appropriate filter (FIG. 16).

The capture devices with the captured DNA were removed from the preformed gel and visualized under UV light. The capture membranes were individually eluted into collection tubes with 6×50 ul buffer washes.

Example 2

Figure 17:
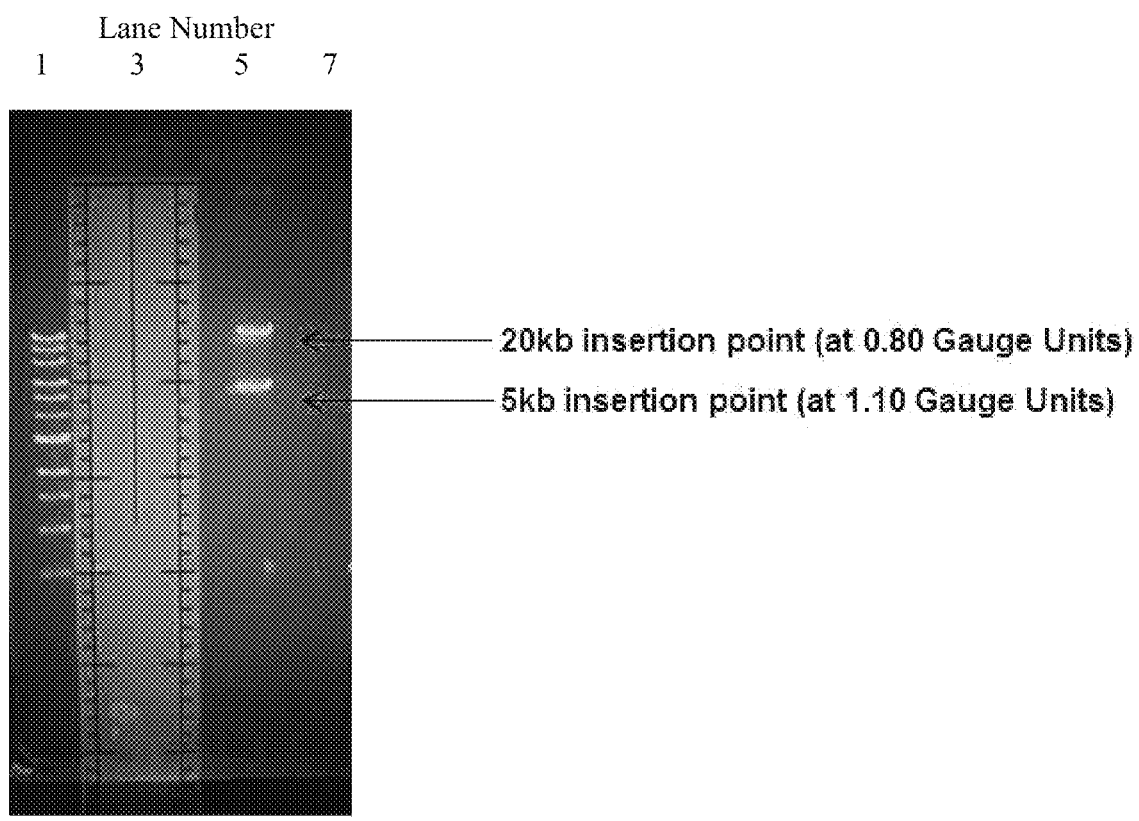
FIG. 17 is a photograph of an unstained gel under blue light following a first electrophoresis of two prelabeled samples and two unlabeled samples with a migration gauge in place, alongside Lane 1 (20 kb DNA and 1 kb DNA Ladder) showing the predetermined distances and placement of capture membranes to capture 5 kb and 20 kb DNA fragments.

Four samples were prepared for agarose gel electrophoresis:
A. 100 ng of 20 kb DNA fragment, 500 ng of 1 kb DNA Ladder and 0.5 ul of SYBR Gold solution
B. 1 ug 5 kb DNA fragment
C. 100 ng 20 kb DNA fragment, 100 ng 5 kb DNA fragment and 0.5 ul of SYBR Gold solution
D. 1 ug 20 kb DNA fragment Samples A-D were loaded into lanes 1, 3, 5 and 7 of an 8-well 0.8% agarose gel, respectively. Gel electrophoresis was run at 100V for 45 minutes. The preformed gel tray with gel was removed from the electrophoresis chamber and was placed over a blue light source and visualized using an orange filter. A migration gauge was placed onto the preformed gel, and notations were made, using the indicia on the gauge, of the migration positions of the 5 kb and 20 kb standards in lane 5 (FIG. 17). From these migration positions, insertion locations for the locator tabs were determined, so as to capture a 5 kb band and a 20 kb band. The preformed gel tray, with gel and migration gauge, was moved to room light and the locator tabs were placed into lanes 3 and 7 of the preformed gel, in locations so as to capture a 5 kb and a 20 kb band, respectively. Capture devices, including capture membranes and rigid support members (each attached along one side of the capture membrane in an adhered strip) were then inserted in front of the locator tabs. Locator tabs were removed, leaving the capture devices in place in the preformed gel.

Figure 18:
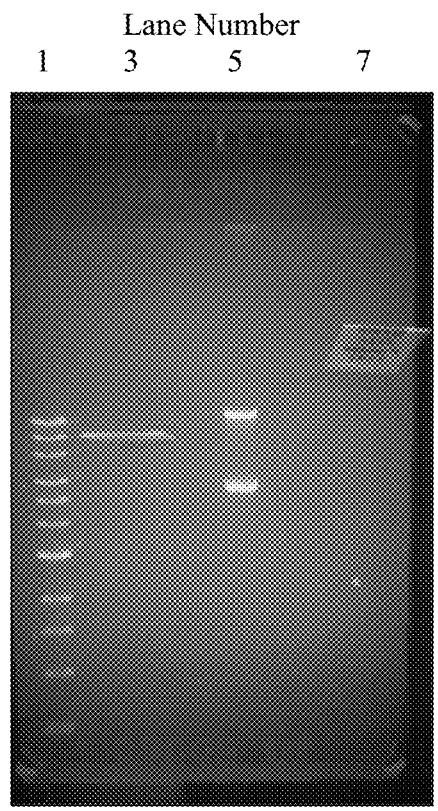
FIG. 18 is a photograph of an unstained gel under blue light following a second electrophoresis of two prelabeled samples and two unlabeled samples with two capture devices inserted at positions to capture 5 kb and 20 kb fragments based on the migration gauge shown in FIG. 17.

The preformed gel tray, containing the capture devices, was returned to the electrophoresis chamber, and a second electrophoresis was run at 100V for 20 minutes to capture the 5 kb and 20 kb DNA on the capture membranes. The preformed gel tray with gel was removed from the electrophoresis chamber and was placed over a blue light source and visualized using an orange filter (FIG. 18).

Figure 19:
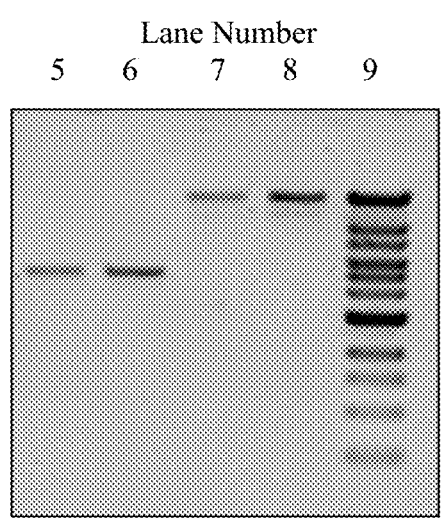
FIG. 19 is a photograph of a pre-stained gel under ultraviolet light following a first electrophoresis of a set of samples containing four samples of DNA eluted from capture membranes in lanes 3 and 7 from the gel shown in FIG. 18, and a DNA ladder standard placed in Lane 9 (shown to estimate the size of the eluted DNA samples in Lanes 5,6,7,8).

The capture devices were removed from the preformed gel, and each of the two capture membranes were individually eluted into collection tubes with 6×50 ul buffer washes. The DNA captured and extracted from capture membranes in lanes 3 and 7 and one DNA ladder standard were analyzed on a 0.8% agarose pre-stained gel containing EtBr run at 100V for 45 minutes. The results are shown in FIG. 19 on a pre-stained gel under ultraviolet light following the first electrophoresis. The details of these samples and lane placement are shown in Table 1.

| Table 1 of Samples Shown in FIG. 19 Analytical Gel | | | | |
|---|---|---|---|---|
| Lane number | 5 | 6 | 7 | 8 | 9 |
| Lane contents | 15 µl of Sample eluted from membrane in Lane 3 | 30 µl of Sample eluted from membrane in Lane 3 | 15 µl of Sample eluted from membrane in Lane 7 | 30 µl of Sample eluted from membrane in Lane 7 | 20 kb DNA Standard and 1 kb DNA ladder |

Example 3

Figure 20:
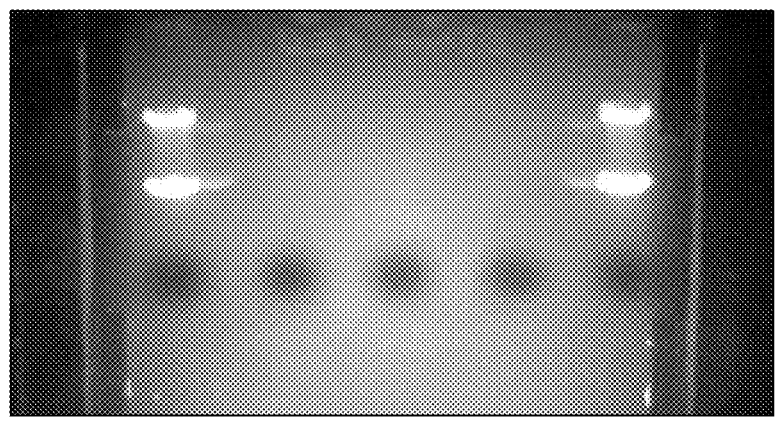
FIG. 20 is a photograph of an unstained gel under blue light following a first electrophoresis of two prelabeled samples and three unlabeled samples; Lane 3 is 20 kb and 5 kb DNA plus SYBR Gold; Lane 5 is 20 kb and 5 kb DNA; Lane 7 is 20 kb and 5 kb DNA; Lane 9 is 20 kb and 5 kb DNA; Lane 11 is 20 kb and 5 kb DNA plus SYBR Gold.
Figure 21:
FIG. 21 is photograph of the same unstained gel as in FIG. 20 under blue light following a first electrophoresis of a set of samples containing two prelabeled samples and three unlabeled samples, with a locator tab in place at a location in Lane 5 to capture a 20 kb DNA band based on straight edge location tool.
Figure 22:
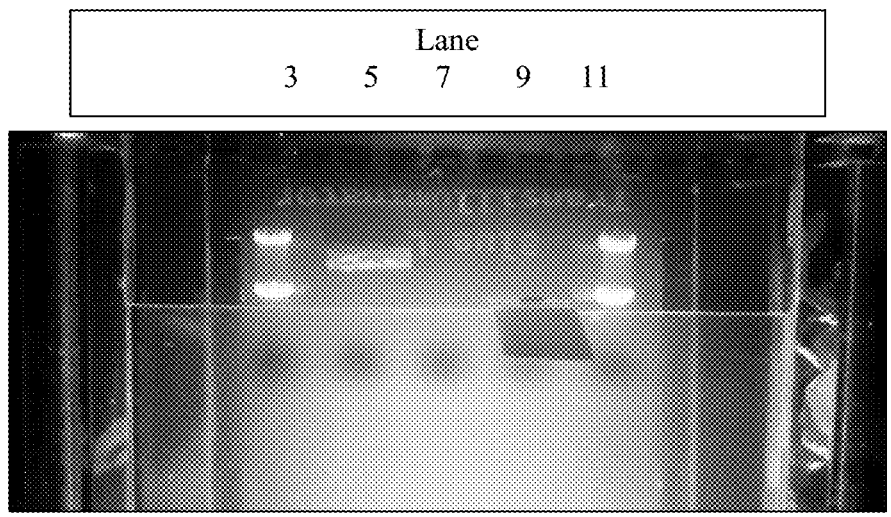
FIG. 22 is a photograph of the same unstained gel as in FIGS. 20 and 21 under blue light following a first electrophoresis of a set of samples containing two prelabeled samples and three unlabeled samples, with a straight edge location tool aligned with 5 kb DNA labeled band and two locator tabs in place, one to capture the 20 kb DNA band and the second to capture the 5 kb band.
Figure 23:
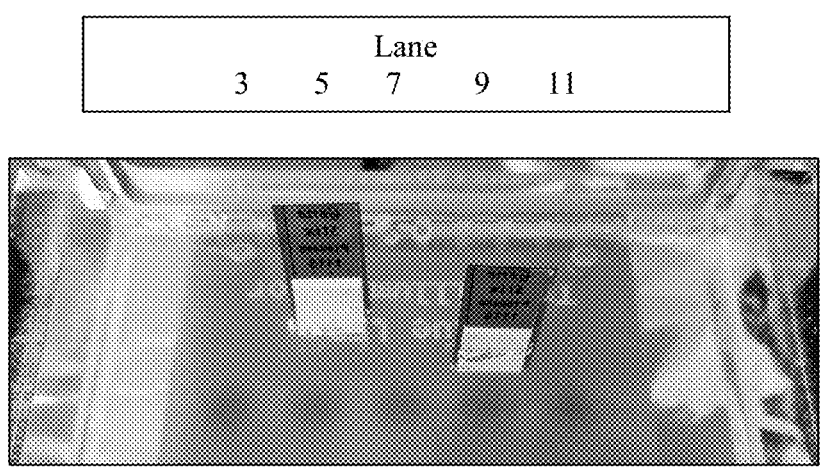
FIG. 23 is a photograph of the same unstained gel as in FIGS. 20-22 in normal light following a first electrophoresis of a set of samples containing two prelabeled samples and three unlabeled samples, with locator tabs and capture devices inserted at locations to capture 5 kb and 20 kb DNA fragments using alignment with a straight edge location tool.

Five samples were prepared for agarose gel electrophoresis:
- A. 1 ug of 20 kb DNA fragment, 1 ug of 5 kb DNA fragment and 0.5 ul of SYBR Gold solution
- B. 1 ug of 20 kb DNA fragment and 1 ug of 5 kb DNA fragment
- C. 1 ug of 20 kb DNA fragment and 1 ug of 5 kb DNA fragment
- D. 1 ug of 20 kb DNA fragment and 1 ug of 5 kb DNA fragment
- E. 1 ug of 20 kb DNA fragment, 1 ug of 5 kb DNA fragment and 0.5 ul of SYBR Gold solution Samples A-E above were loaded into lanes 3, 5, 7, 9 and 11 of a 14-well 0.8% agarose gel, respectively. Gel electrophoresis was run at 100V for 45 minutes. The preformed gel tray with gel was removed from the electrophoresis chamber and was placed over a blue light source and visualized using an orange filter (FIG. 20). A straight edge was placed across the preformed gel, and aligned with the 20 kb markers in lanes 3 and 11 so as to guide the placement position for a locator tab in lane 5 for capture of a 20 kb band. The locator tab was inserted into the preformed gel at a location in lane 5 based on the straight edge location (FIG. 21). The straight edge was then placed across the preformed gel, and aligned with the 5 kb markers in lanes 3 and 11 so as to guide the placement position for a locator tab in Lane 9 for later capture of a 5 kb band. The second locator tab was inserted into the preformed gel (FIG. 22). The preformed gel tray, with gel and locator tabs, was moved to room light and capture devices, including capture membranes and support members, were then inserted in front of the locator tabs (FIG. 23).

Figure 24:
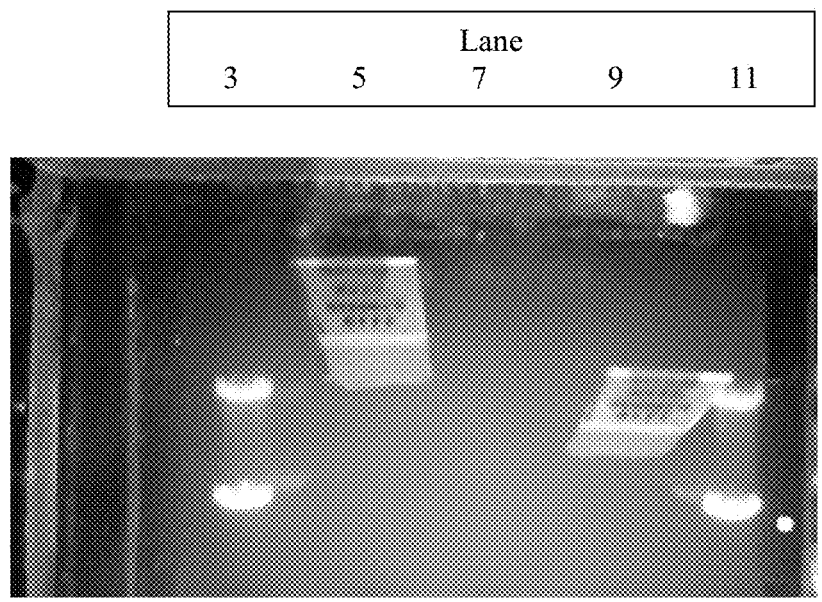
FIG. 24 is a photograph of an unstained gel as in FIG. 23 under blue light following a second electrophoresis of a set of samples containing two prelabeled samples and three unlabeled samples with capture devices, including capture membranes and support membranes, at locations to capture 5 kb and 20 kb fragments based on alignment with a straight edge.

Locator tabs were removed, leaving the capture devices in place in the preformed gel. The preformed gel tray, containing the capture devices, was returned to the electrophoresis chamber, and a second electrophoresis was run at 100V for 20 minutes in the same direction as the first electrophoresis to capture the 5 kb and 20 kb DNA on the capture membranes. The preformed gel tray with gel was removed from the electrophoresis chamber and was placed over a blue light source and visualized using an orange filter (FIG. 24).

Figure 25:
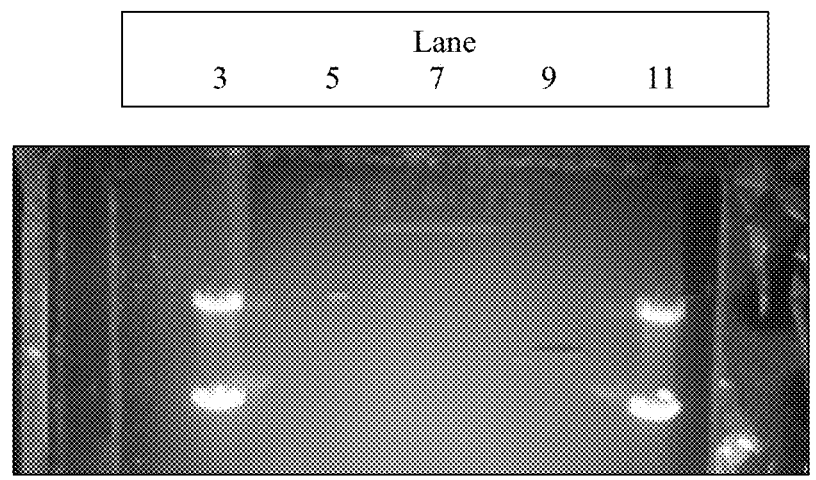
FIG. 25 is a photograph of an unstained gel as in FIG. 24 under blue light following a second electrophoresis of a set of samples containing two prelabeled samples and three unlabeled samples after removal of capture devices at locations to capture 5 kb and 20 kb fragments based on alignment with a straight edge.

The capture devices were then removed from the preformed gel (FIG. 25), and each of the two capture membranes were individually eluted into collection tubes with 6×50 ul buffer washes. Collected samples were analyzed on a 0.8% agarose pre-stained gel containing EtBr and run at 100V for 45 minutes.

Figure 26:
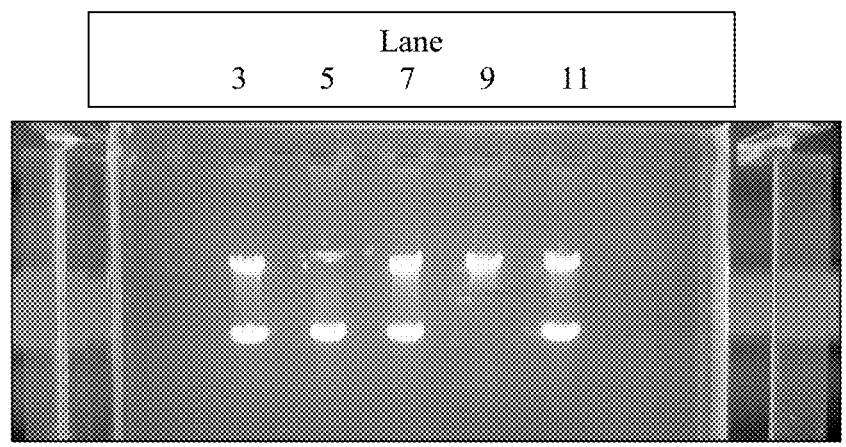
FIG. 26 is a photograph of a gel of FIGS. 24 and 25 viewed under UV light following a second electrophoresis of the set of samples, i.e., two prelabeled samples and three unlabeled samples, after removal of the capture devices and soaking in EtBr.

Following removal of the capture devices, the preformed gel was stained with an EtBr solution, rinsed with water and the preformed gel placed over a UV light source and visualized using the appropriate filter (FIG. 26). FIG. 26 shows that the one band from lane 5 and one from lane 9 have been extracted from the gel.

Example 4

Figure 27:
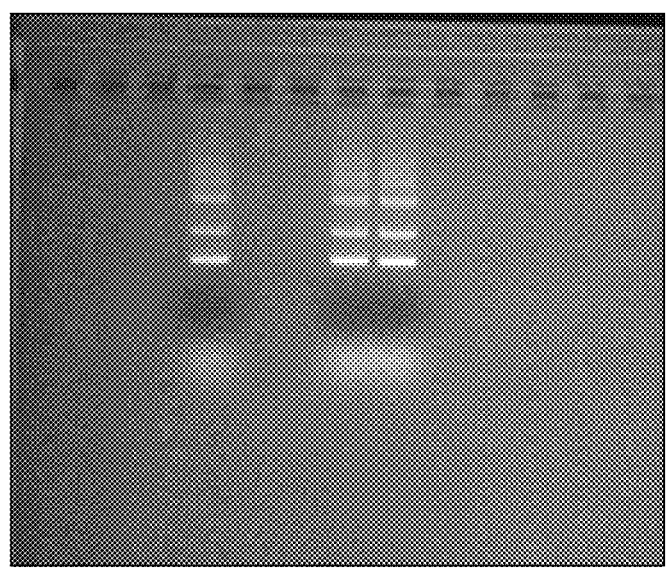
FIG. 27 is a photograph of a pre-stained gel containing EtBr and three samples following a first electrophoresis in a first direction.
Figure 28:
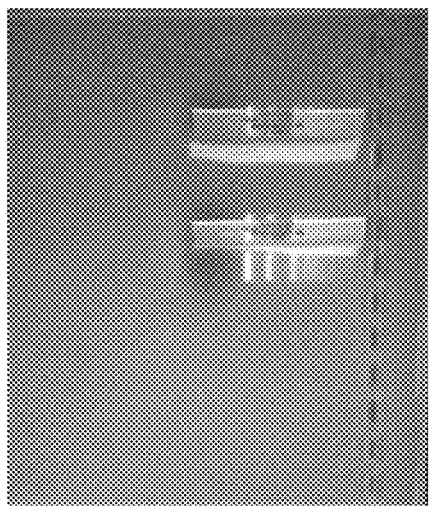
FIG. 28 is a photograph of a pre-stained gel containing EtBr of FIG. 27 with two capture devices placed in a position immediately to the right of, and perpendicular to the bands containing the DNA fragments, with the gel being rotated 90 degrees.
Figure 29:
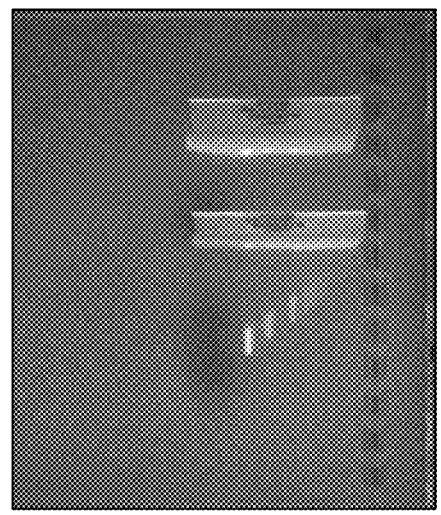
FIG. 29 is a photograph of the pre-stained gel containing EtBr with two capture devices of FIG. 28 following a second electrophoresis for 30 minutes in a direction perpendicular to the direction of the first electrophoresis.

Three samples were prepared for agarose gel electrophoresis:
- A. 500 ng of Reverse Mass DNA Ladder
- B. 500 ng of Reverse Mass DNA Ladder
- C. 500 ng of Reverse Mass DNA Ladder Samples A-C above were loaded into lanes 4, 7 and 8, respectively, of a 14-well 1.0% agarose pre-stained gel containing EtBr. A first gel electrophoresis was run at 100V for 45 minutes in a first direction. The preformed gel tray with gel was removed from the electrophoresis chamber and was placed over a UV light source and visualized using the appropriate filter (FIG. 27). Two locator tabs were placed in the preformed gel in a position immediately to the right of, and perpendicular to the bands containing the DNA fragments in lanes 4 and 7. The preformed gel tray, containing the locator tabs, was removed from the UV light and moved to visible light. Capture devices, including capture membranes and rigid support members (each attached along one side of the capture membrane in an adhered strip) were then inserted adjacent to the locator tabs and the locator tabs were removed, leaving the capture devices in place in the preformed gel. The bottom portion of the preformed gel was cut off and the top portion of the preformed gel was reoriented in the gel tray for orthogonal electrophoresis. The gel tray and the preformed gel, containing the capture devices, was visualized over a UV light source (FIG. 28) and then returned to the electrophoresis chamber. A second electrophoresis was run at 100V for 30 minutes in a direction perpendicular to the first electrophoresis direction to capture the Reverse Mass DNA Ladder from lanes 4 and 7 on the capture membranes. The preformed gel tray with gel was removed from the electrophoresis chamber and was placed over a UV light source and visualized using the appropriate filter (FIG. 29).

The capture devices were removed from the preformed gel and visualized under UV light. Individual bands, visible on the capture membrane, were cut from the capture membrane and eluted into collection tubes.

Example 5

Figure 30:
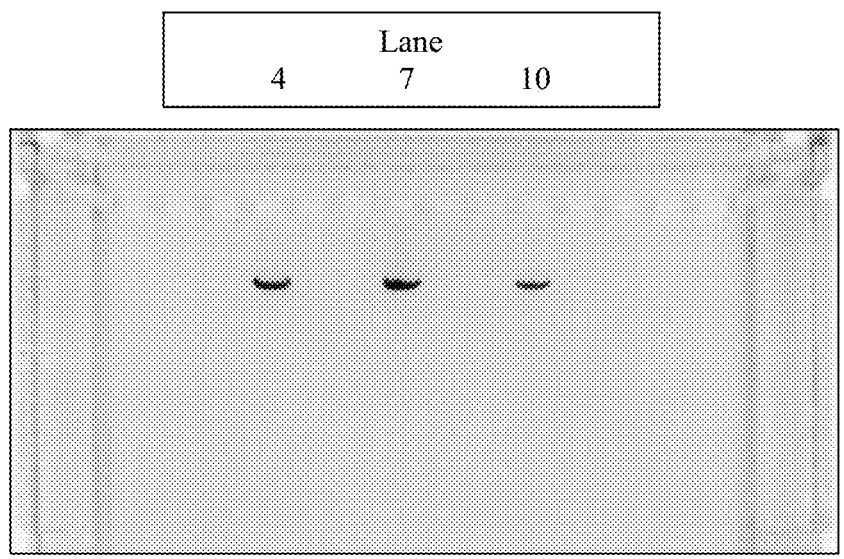
FIG. 30 is a photograph viewed under UV light of a pre-stained gel containing EtBr and three samples (Lane 4 is 600 ng 5 kb DNA fragment; Lane 7 is 600 ng 5 kb DNA fragment; Lane 10 is 300 ng 5 kb DNA fragment) following a first electrophoresis.
Figure 31:
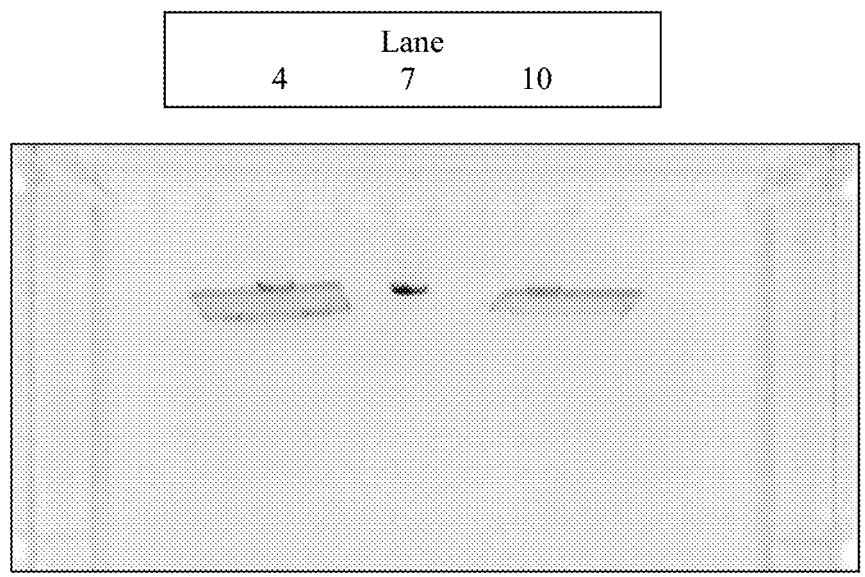
FIG. 31 is a photograph of the pre-stained gel of FIG. 30 containing EtBr viewed under UV light with two capture devices inserted into the gel at locations to capture a 5 kb fragment in Lanes 4 and 10.

Three samples were prepared for agarose gel electrophoresis:
- A. 600 ng of 5 kb DNA fragment
- B. 600 ng of 5 kb DNA fragment
- C. 300 ng of 5 kb DNA fragment Samples A-C above were loaded into lanes 4, 7 and 10, respectively, of a 14-well 0.8% agarose pre-stained gel containing EtBr. A first gel electrophoresis was run at 100V for 40 minutes. The preformed gel tray with gel was removed from the electrophoresis chamber and was placed over a UV light source and visualized using the appropriate filter (FIG. 30). Capture devices, including capture membranes and support members attached on four sides (thereby making a fully rigid capture device), were then inserted directly into the preformed gel, in lanes 4 and 10 of the preformed gel, at locations so as to capture a 5 kb band in those lanes (FIG. 31).

The preformed gel tray, containing the rigid capture devices, was returned to visible light and placed in the electrophoresis chamber, and a second electrophoresis was run at 100V for 30 minutes in the same direction as the first electrophoresis to capture the 5 kb band on the capture membranes. The preformed gel tray with gel was removed from the electrophoresis chamber.

Figure 32:
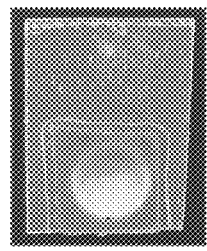
FIG. 32 is a photograph of the capture device from Lane 4 in FIG. 31, viewed under UV light, after a second electrophoresis and removal from the pre-stained gel, having captured the 5 kb DNA fragment.

The rigid capture devices were removed from the preformed gel and visualized under UV light. One rigid capture device with the 5 kb band capturing thereon is shown in FIG. 32. The capture membranes were individually eluted into collection tubes with 6×50 ul buffer washes.

Figure 35:
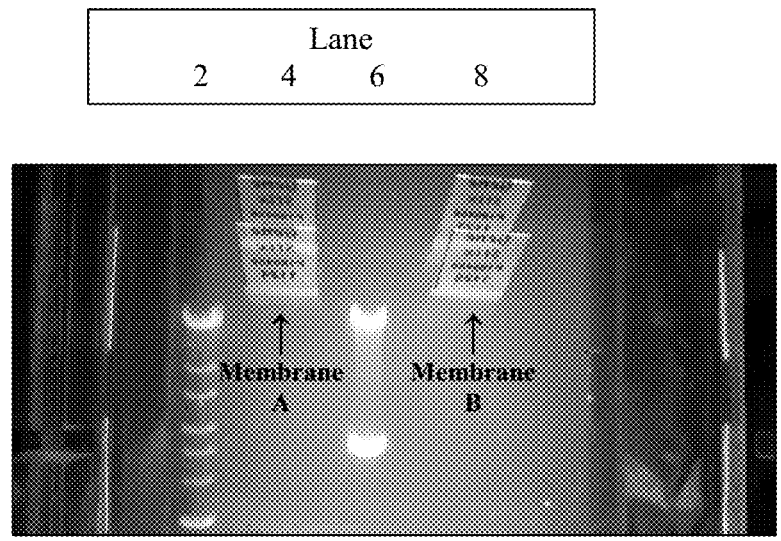
FIG. 35 is a photograph of the unstained gel of FIG. 34 after insertion of capture devices at locations in Lanes 4 and 8 to capture bands greater than 3 kb and capture bands greater than 6 kb following a second electrophoresis.

Locator tabs were removed, leaving the capture membranes in place in the gel. The gel tray, containing the capture devices, was returned to the electrophoresis chamber, and a second electrophoresis was run at 100V for 60 minutes in the same direction as the first electrophoresis to capture the DNA bands greater than 3 kb and including bands up to 6 kb on one pair of membranes (membranes A and B) while capturing and thus blocking DNA bands greater than 6 kb from reaching those membranes. The gel tray with gel was removed from the electrophoresis chamber and was placed over a blue light source and visualized using an orange filter (FIG. 35).

Figure 36:
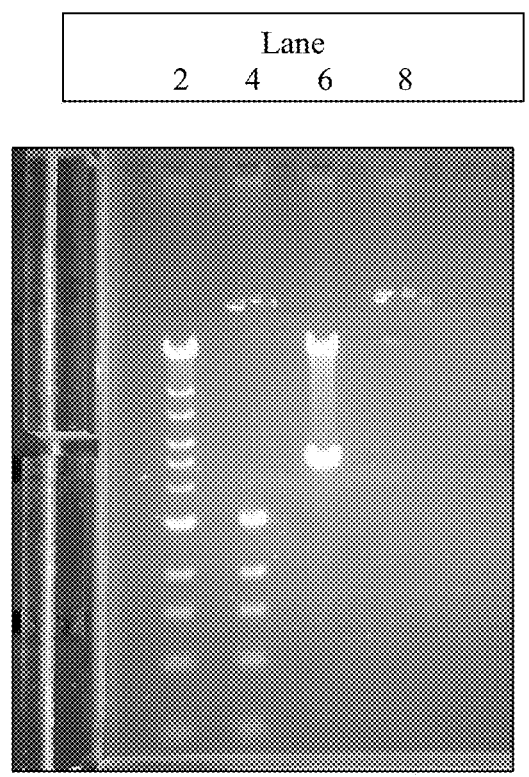
FIG. 36 is a photograph of the gel in FIG. 35 after removal of 4 capture devices and soaking the gel in EtBr and viewing in UV light, showing the DNA that remains in the gel.

The membranes (A and B) were removed from the gel and the gel was stained with an EtBr solution, rinsed with water, placed over a UV light source, and visualized using the appropriate filter (FIG. 36).

Figure 37:
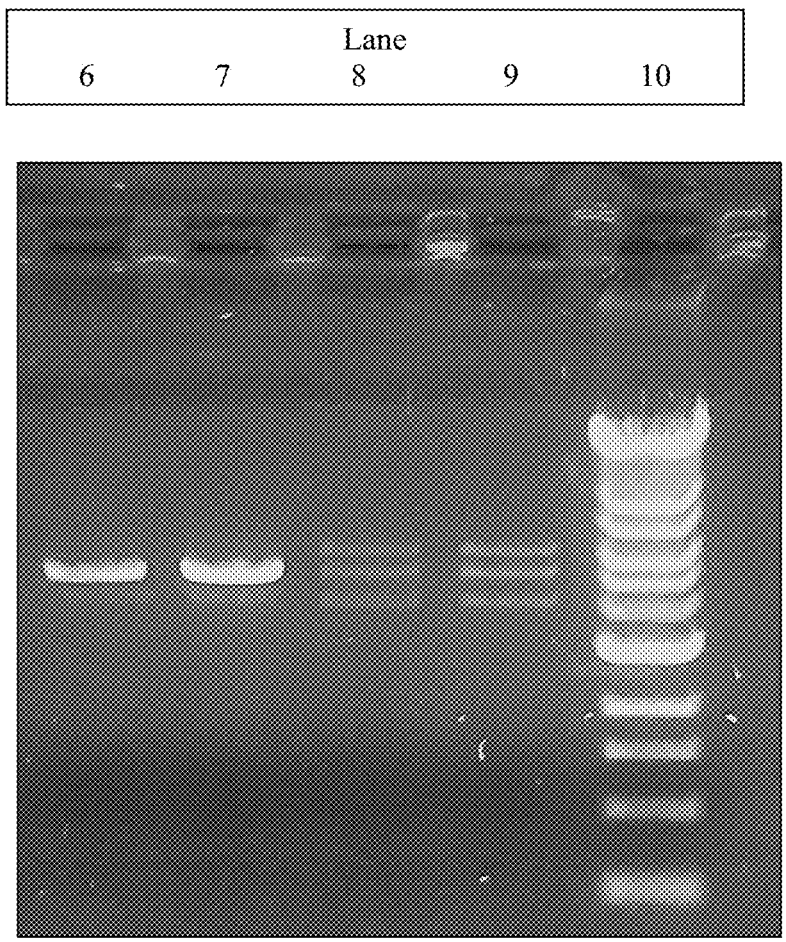
FIG. 37 is a photograph of an EtBr pre-stained gel under ultraviolet light following a first electrophoresis of a set of samples containing four samples of DNA extracted from membranes A and B in Lanes 4 and 8 from the gel shown in FIG. 35, and one DNA ladder standard in Lane 10.

The two membranes removed from the gel (membranes A and B) were individually eluted into collection tubes with 6×50 ul buffer washes. Collected samples were analyzed on a 0.8% agarose pre-stained gel containing EtBr run at 100V for 45 minutes. The results are shown in FIG. 37 on a pre-stained gel under ultraviolet light following the first electrophoresis. The details of these samples and lane placement are shown in Table 2.

| | Table 2 of Samples Shown in FIG. 37 Analytical Gel | | | | |
|---|---|---|---|---|---|
| Lane number | 6 | 7 | 8 | 9 | 10 |
| Lane contents | 15 µl of Sample eluted from membrane B in Lane 8 | 30 µl of Sample eluted from membrane B in Lane 8 | 15 µl of Sample eluted from membrane A in Lane 4 | 30 µl of Sample eluted from membrane A in Lane 4 | 20 kb DNA Standard and 1 kb DNA ladder |

Example 6

Figure 33:
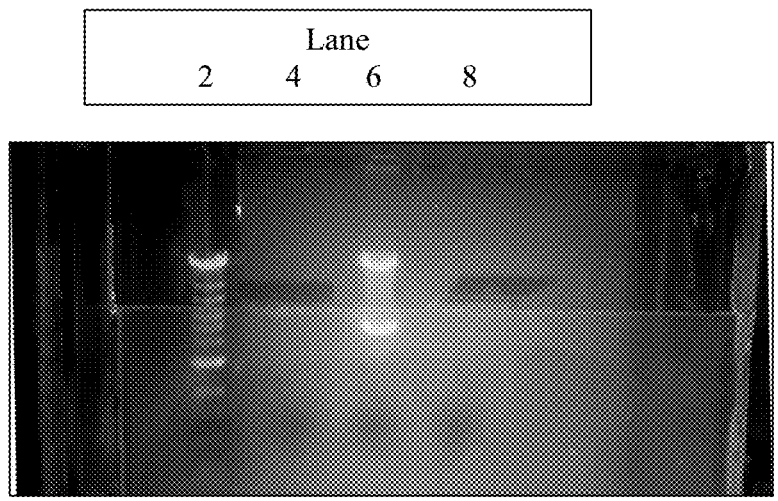
FIG. 33 is a photograph of an unstained gel under blue light following a first electrophoresis of two prelabeled samples and two unlabeled samples, with a straight edge aligned at a position slightly greater than a 6 kb DNA labeled band, and with locator tabs at positions in Lanes 4 and 8 for capture of bands greater than 6 kb.
Figure 34:
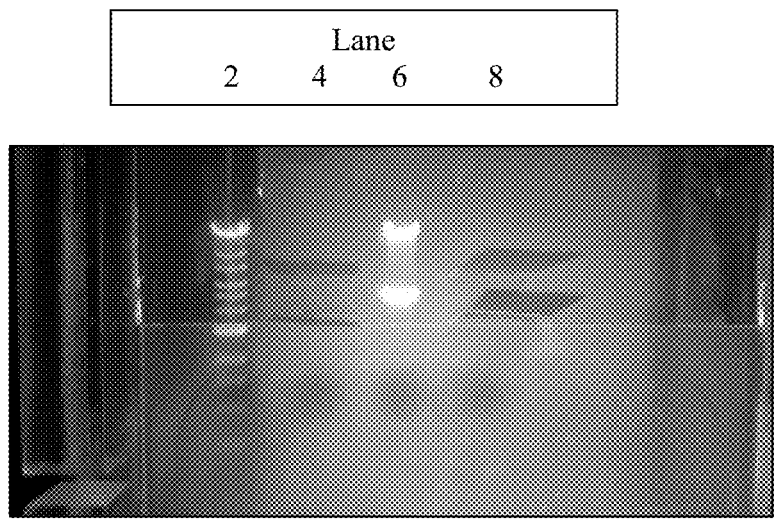
FIG. 34 is a photograph of the unstained gel following a first electrophoresis of FIG. 33, with a straight edge aligned at a position slightly greater than a 3 kb DNA labeled band, and with locator tabs at positions in Lanes 4 and 8 for capture of bands greater than 3 kb and capture of bands greater than 6 kb.

Four samples were prepared for agarose gel electrophoresis:
A. 1 ug of 20 kb DNA fragment, 1 ug of 1 kb DNA ladder and 0.5 ul of SYBR Gold solution
B. 1 ug of 20 kb DNA fragment and 1 ug of 1 kb DNA ladder
C. 1 ug of 20 kb DNA fragment, 1 ug of 5 kb DNA fragment and 0.5 ul of SYBR Gold solution
D. 1 ug of 20 kb DNA fragment and 1 ug of 5 kb DNA fragment Samples A-D above were loaded into lanes 2, 4, 6 and 8 of a 14-well 0.8% agarose gel, respectively. A first gel electrophoresis was run at 100V for 60 minutes. The gel tray with gel was removed from the electrophoresis chamber and was placed over a blue light source and visualized using an orange filter. A straight edge was placed across the gel, and aligned at a position slightly greater than the 6 kb marker in lane 1 so as to guide the placement position for locator tabs in lanes 4 and 8 for later capture of bands greater than 6 kb. Locator tabs were inserted into the gel (FIG. 33). The straight edge was then placed across the gel, and aligned at a position slightly less than the 4 kb marker in lane 1 so as to guide the placement position for locator tabs in lanes 4 and 8 for later capture of bands greater than 3 kb. Locator tabs were inserted into the gel (FIG. 34). Capture devices, including capture membranes and rigid support members (each attached along one side of the capture membrane in an adhered strip), were then inserted in front of the locator tabs.

While there have been described what are presently believed to be the certain desirable embodiments of the invention, those skilled in the art will realize that changes and modifications may be made thereto without departing from the spirit of the invention, and it is intended to include all such changes and modifications as fall within the true scope of the invention.

What is claimed is:

1. A method of collecting one or more target macromolecules in a capture membrane, comprising the steps of:
   a) introducing a sample containing a mixture of macromolecules into a sample well at a position on a preformed gel;
   b) applying a first electric field for a first amount of time in a first direction across opposing ends of the preformed gel;
   c) stopping the first electric field when the mixture of macromolecules in the sample have separated along the preformed gel;
   d) identifying a position in the preformed gel of the target macromolecule;
   e) inserting an insertion guide comprising a locator tab into the preformed gel at the position in the preformed gel in a future pathway of the target macromolecule;
   f) creating a slit in said preformed gel using the insertion guide with no or minimal damage to said preformed gel;

g) guiding a capture device comprising the capture membrane into the preformed gel along the insertion guide thereby inserting the capture device into said slit;
h) applying a second electric field for a second amount of time in a second direction to the preformed gel in the direction of the inserted capture device; and
i) stopping the second electric field when the target macromolecule is collected in the capture membrane.

2. The method of claim 1, further comprising the steps of:
(j) removing the capture device from the preformed gel, and
(k) processing the capture membrane.

3. The method of claim 2, further including the step of: (l) recovering the target macromolecule from the capture membrane.

4. The method of claim 1, wherein in step (d), a migration gauge is used to identify the position of the target macromolecule on the preformed gel.

5. The method of claim 1, after the step of inserting the capture device into the preformed gel, further comprising the step of removing said insertion guide from said preformed gel.

6. The method of claim 1, wherein the insertion guide comprises an inert plastic.

7. The method of claim 6, wherein the insertion guide has one or more sharp corners or edges and is of sufficient rigidity to pierce the preformed gel with one of said one or more sharp corners or edges.

8. The method of claim 1, wherein said insertion guide and said well form an angle of from about 0° to about 90°.

9. The method of claim 1, wherein the capture membrane is removably attached or adhered to a support member, wherein the support member provides increased structural rigidity to the capture membrane.

10. The method of claim 9, wherein the support member is rigid.

11. The method of claim 9, wherein said support member includes a handle.

12. The method of claim 9, wherein said support member includes written indicia.

13. The method of claim 12, wherein said written indicia comprises gauge markings correlating to a migration distance.

14. The method of claim 1, wherein said target macromolecule is selected from the group consisting of: a radioactively labeled macromolecule, chromophorically labeled macromolecule, fluorophorically labeled macromolecule, stained macromolecule, unlabeled macromolecule, and any combination thereof.

15. The method of claim 1, wherein said target macromolecule is selected from the group consisting of: DNA, RNA, proteins, polypeptides, amino acid chains, polysaccharides, oligosaccharides, any fragments thereof, and any combination thereof.

16. The method of claim 1, further comprising the steps of:
after step d), identifying a position in the preformed gel of a second target macromolecule;
inserting an insertion guide comprising a locator tab into the preformed gel at the position in the preformed gel in a future pathway of the second target macromolecule;
creating a slit in said preformed gel using the insertion guide with no or minimal damage to said preformed gel; and
guiding a second capture device comprising a second capture membrane into the preformed gel along the insertion guide thereby inserting the second capture device into said slit;
wherein, by applying the electric field for the second amount of time to the preformed gel, the second target macromolecule moves in the direction of the inserted second capture device and is collected in the second capture membrane.

17. The method of claim 16, further comprising the steps of:
removing said second capture device from said preformed gel, and
processing the second capture membrane.

18. A kit for macromolecule isolation and recovery comprising:
a. a preformed gel;
b. a capture device comprising a capture membrane removably attached or adhered to a support member;
c. an insertion guide comprising a locator tab; and
d. a migration gauge.

* * * * *